US006210707B1

(12) United States Patent
Papahadjopoulos et al.

(10) Patent No.: US 6,210,707 B1
(45) Date of Patent: Apr. 3, 2001

(54) METHODS OF FORMING PROTEIN-LINKED LIPIDIC MICROPARTICLES, AND COMPOSITIONS THEREOF

(75) Inventors: Demetrios Papahadjopoulos; Keelung Hong; Weiwen Zheng; Dmitri B. Kirpotin, all of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/076,618

(22) Filed: May 12, 1998

Related U.S. Application Data

(63) Continuation-in-part of application No. 08/967,791, filed on Nov. 10, 1997.
(60) Provisional application No. 60/030,578, filed on Nov. 12, 1996.

(51) Int. Cl.$^7$ .................................................. A61K 9/127

(52) U.S. Cl. .............................. 424/450; 435/6; 435/7.1; 435/7.2; 435/440

(58) Field of Search ................................ 424/450; 435/6, 435/7.1, 7.2, 440

(56) References Cited

U.S. PATENT DOCUMENTS 5,459,127 * 10/1995 Felgner et al. .
5,681,940 * 10/1997 Wang et al. .
5,783,210 * 7/1998 Tremblay et al. .

FOREIGN PATENT DOCUMENTS

WO 98/02454   1/1998 (WO) .

OTHER PUBLICATIONS

Zalipsky et al., "Poly(ethyene glycol)–Grafted Liposomes with Oligopeptide or Oligosaccharide Ligands Appended to the Termini of the Polymer Chains", *Bioconjugate Chem.*, 8:111–118 (1997).*
Blaese, et al., "Vectors in Cancer Therapy: How Will They Deliver?" *Cancer Gene Therapy*, 2(4):291–197 (1995).*
Crystal et al., "Transfer of Genes of Humans: Early Lessons and Obstacles to Success," *Science* 270:404–410 (1995).*
Gao et al., "Cationic Liposome–Miediated Gene Transfer," *Gene Therapy* , 2:710–722 (1995).*
Behr, "Gene Transfer with Synthetic Cationic Amphiphiles: Prospects for Gene Therapy," *Bioconjugate Chem.*, 5:382–389 (1994).*
Remy et al., "Gene Transfer with a Series of Lipophilic DNA–Binding Molecules," *Bioconjugate Chem.*, 5:647–654 (1994).*
Plum et al., "Condensation of DNA by Trivalent Cations. 2 Effects of Cation Structure," *Biopolymers,* 30:631–643 (1990).*

Allen et al., "Liposomes Containing Synthetic Lipid Derivatives of Poly(Ethylene Glyocol) Show Prolonged Circulation Half–Lives In Vivo," *Biochimica et Biophysica Acia*. 1066:29–36 (1991).*
Papahadjopoulos et al., "Sterically Stabilized Liposomes: Improvements in Pharmacokinetics and Antitumor Therapeutic Efficacy," Proc. Nat'l Acad. Sci USA, 88:11460–11464 (1991).*
Ahmad et al., "Antibody–Mediated Specific Binding and Cytotoxicity of Liposome–Entrapped Doxoribicun to Lung Cancer Cells in Vitro," *Cancer Research* , 52:4817–4820 (1992).*
Martin et al, "Irreversible Coupling of Immunoglobulin Fragments to Performed Vesicles," *J. of Biological Chemistry* , 257(1):286–288 (1982).*
Szoka Jr. et al., "Procedure for Preparation of Liposomes with Large Internal Aqueous Space and High Capture by Reverse–Phase Evaporation," Proc. Nat'l. Acad. Sci. USA, 75(9):4194–4196 (1978).*
Felgner et al., "Lipofection: A High Efficient, Lipid–Mediated Dan–Transfection Procedure," *Proc. Nat'l Acad. Sci. USA,* 84:7413–7417 (1987).*
Felgner et al., "Enhanced Gene Delivery and Mechanism Studies With a Novel Series of Cationic Lipid Formulations," *J. Biological Chemistry* , 269(4):2550–2561 (1994).*
Liu et al., "Cationic Liposome–Mediated Intravenous Gene Delivery," *J. Biological Chemistry,*270(42):24864–24870 (1995).*
Mayhew et al., "Role of Cholesterol in Enhancing the Antitumore Activity of Cytosine Arabinoside Entrapped in Liposomes," *Cancer Treatment Reports,* 63(11–12):1923–1928 (1979).*

(List continued on next page.)

*Primary Examiner*—James Ketter
(74) *Attorney, Agent, or Firm*—Townsend and Townsend and Crew LLP

(57) ABSTRACT

The present invention provides for lipid:nucleic acid complexes that have increased shelf life and high transfection activity in vivo following intravenous injection, and methods of preparing such complexes. The methods generally involve contacting a nucleic acid with an organic polycation to produce a condensed nucleic acid, and then combining the condensed nucleic acid with a lipid comprising an amphiphilic cationic lipid to produce the lipid:nucleic acid complex. This complex can be further stabilized by the addition of a hydrophilic polymer attached to hydrophobic side chains. The complex can also be made specific for specific cells, by incorporating a targeting moiety such as an Fab' fragment attached to a hydrophilic polymer. The present invention further relates to lipidic microparticles with attached proteins which have been first conjugated to linker molecules having a hydrophilic polymer domain and a hydrophobic domain capable of stable association with the microparticle, or proteins which have been engineered to contain a hydrophilic domain and a lipid moiety permitting stable association with the microparticle.

46 Claims, 4 Drawing Sheets

OTHER PUBLICATIONS

Zhu et al., "Systemic Gene Expression After Intravenous DNA Delivery into Adult Mice," *Science*, 26:209–211 (1993).*

Solodin et al., "A Novel Series of Amphiphilic Imidazolinium Compounds for In Vitro and In Vivo Gene Delivery," *Biochemistry*, 34:13537–12544 (1995).*

Thierry et al., "Systematic Gene Therapy: Biodistribution and Long–Term Expression of a Transgene in Mice," Proc. Nat'l. Acad. Sci. USA, 92:9741–9746 (1995).*

Carter et al., "High–Level *Escherichia Coli* Expression and Production of a Bivalent Humanized Antibody Fragment," *Biotechnology*, 10:163–167 (1992).*

Hofland et al., "Formation of Stable Cationic Lipid/DNA Complexes For Gene Transfer," Proc. Nat'l. Acad. Sci USA, 93:7305–7309 (1996).*

Hansen et al., *BBA*, vol. 1239, 1995, pp. 133–144.*

* cited by examiner

METHODS OF FORMING PROTEIN-LINKED LIPIDIC MICROPARTICLES, AND COMPOSITIONS THEREOF

CROSS REFERENCE TO RELATED APPLICATIONS

This application is a continuation-in-part of U.S. Ser. No. 08/967,791, filed Nov. 10, 1997, and of Provisional Application U.S. Ser. No. 60/030,578, filed Nov. 12, 1996, both of which are incorporated herein by reference.

FEDERALLY SPONSORED RESEARCH OR DEVELOPMENT

Not applicable.

FIELD OF THE INVENTION

The present invention relates to the field of cationic lipid:DNA complexes ("CLDC"). In particular, the present invention relates to lipid:nucleic acid complexes that contain (1) hydrophilic polymer; (2) nucleic acid that has been condensed with organic polycations; and (3) hydrophilic polymer and nucleic acid that has been condensed with organic polycations. The lipid:nucleic acid complexes of this invention show high transfection activity in vivo following intravenous injection and an unexpected increase in shelf life, as determined by in vivo transfection activity.

The present invention further relates to the field of lipidic microparticles, such as liposomes, lipid:DNA complexes, lipid:drug complexes, and microemulsion droplets, attached to proteins. In particular, the invention relates to lipidic microparticles with attached proteins which have been first conjugated to linker molecules having a hydrophilic polymer domain and a hydrophobic domain capable of stable association with the microparticle, or proteins which have been engineered to contain a hydrophilic domain and a lipid moiety permitting stable association with a lipidic microparticle.

BACKGROUND OF THE INVENTION

Liposomes that consist of amphiphilic cationic molecules are useful non-viral vectors for gene delivery in vitro and in vivo (reviewed in Crystal, *Science* 270: 404–410 (1995); Blaese et al., *Cancer Gene Ther.* 2: 291–297 (1995); Behr et al., *Bioconjugate Chem.* 5: 382–389 (1994); Remy et al., *Bioconjugate Chem.* 5: 647–654 (1994); and Gao et al., *Gene Therapy* 2: 710–722 (1995)). In theory, the positively charged liposomes complex to negatively charged nucleic acids via electrostatic interactions to form lipid:nucleic acid complexes. The lipid:nucleic acid complexes have several advantages as gene transfer vectors. Unlike viral vectors, the lipid:nucleic acid complexes can be used to transfer expression cassettes of essentially unlimited size. Since the complexes lack proteins, they may evoke fewer immunogenic and inflammatory responses. Moreover, they cannot replicate or recombine to form an infectious agent and have low integration frequency.

There are a number of publications that demonstrate convincingly that amphiphilic cationic lipids can mediate gene delivery in vivo and in vitro, by showing detectable expression of a reporter gene in culture cells in vitro (Feigner et al., *Proc. Natl. Acad. Sci. USA* 84: 7413–17 (1987); Loeffler et al., *Methods in Enzymology* 217: 599–618 (1993); Felgner et al., *J. Biol. Chem.* 269: 2550–2561 (1994)). Because lipid:nucleic acid complexes are on occasion not as efficient as viral vectors for achieving successful gene transfer, much effort has been devoted in finding cationic lipids with increased transfection efficiency (Behr, *Bioconjugate Chem.* 5: 382–389 (1994); Remy et al., *Bioconjugate Chem.* 5: 647–654 (1994); Gao et al., *Gene Therapy* 2: 710–722 (1995)). Lipid:nucleic acid complexes are regarded with enthusiasm as a potentially useful tool for gene therapy.

Several groups have reported the use of amphiphilic cationic lipid:nucleic acid complexes for in vivo transfection both in animals, and in humans (reviewed in Gao et al., *Gene Therapy* 2: 710–722 (1995); Zhu et al., *Science* 261: 209–211 (1993); and Thierry et al., *Proc. Natl. Acad. Sci. USA* 92: 9742–9746 (1995)). However, the technical problems for preparation of complexes that have stable shelf-lives have not been addressed. For example, unlike viral vector preparations, lipid:nucleic acid complexes are unstable in terms of particle size (Behr, *Bioconjugate Chem.* 5: 382–389 (1994); Remy et al., *Bioconjugate Chem.* 5: 647–654 (1994); Gao et al., *Gene Therapy* 2: 710–722 (1995)). It is therefore difficult to obtain homogeneous lipid:nucleic acid complexes with a size distribution suitable for systemic injection. Most preparations of lipid:nucleic acid complexes are metastable. Consequently, these complexes typically must be used within a short period of time ranging from 30 minutes to a few hours. In recent clinical trials using cationic lipids as a carrier for DNA delivery, the two components were mixed at the bed-side and used immediately (Gao et al., *Gene Therapy* 2: 710–722 (1995)). The structural instability along with the loss of transfection activity of lipid:nucleic acid complex with time have been challenges for the future development of lipid-mediated gene therapy.

Liposomes consisting of amphiphilic cationic molecules are not, of course, the only form of lipidic microparticles and gene therapy is not the only utility for such particles. Lipidic microparticles have also been used for delivery of drugs and other agents to target sites. Targeting of the microparticles is typically achieved through use of a protein attached to the surface of the microparticle, which may, for example be a ligand for cell surface receptor on a cell type of interest. Conversely, the protein may be an antibody which specifically recognizes an antigen on a cell type of interest, such as diseased cells carrying specific markers. Additionally, proteins can be attached for purposes other than targeting. For example, liposomes can contain prodrugs which slowly seep from the liposome into the circulation. An enzyme attached to the liposome can then convert the prodrug into its active form.

Current methods for effecting the attachment of proteins to lipidic microparticles have been of two types. The first type requires introducing a linker molecule bearing an "active" group (one which reacts with a functional group of the protein) into the microparticle composition prior to conjugation of the "activated" particle with the protein of interest. The disadvantages of methods of this type are: often uncontrollable, incomplete reaction of the protein with the linker; the presence of excess linker on the resulting conjugate, potentially adverse effect of the linker on the stability of the particle, and the inability to incorporate components reactive with the linker into the composition of the particle.

The second group of methods employs the steps of (a) attachment of a hydrophobic moiety, such as a hydrocarbon chain, to the protein molecule, (b) dissolving the components of the lipidic microparticle, along with the conjugate of step (a) in the presence of a detergent, and (c) removing the said detergent, effecting the formation of the lipidic particle incorporating the protein conjugate (Torchilin, *Immunomethods* 4-244–258 (1994); Laukkanen et al., *Biochemistry* 33:11664–11670 (1994)). These methods have a number of disadvantages, including the imposition of severe limitations on the range of methods by which the particle can be formed, (e.g. the detergent removal technique is required) and by which the drug or other agent can be loaded into the microparticle. Moreover, step (b) requires the dissolution of the microparticle. These methods are therefore unable to attach a protein to a premade particle without first destroying it. The presence of detergent in these methods is unavoidable because without a detergent the hydrophobically modified protein is insoluble in aqueous medium The "insertion" into liposomes of hydrophilic polymer-lipid linked to a small (5 amino acid) oligopeptide or small oligosaccharide has been reported. (Zalipsky et al., *Bioconjugate Chem.* 8:111–118 (1997). The peptide and oligosaccharide employed were, however, of a size (molecular weight, 500–3,000 Da) smaller than, or comparable to, the linker itself (molecular weight 2,750 Da). This study therefore provides no guidance for inserting into liposomes or other lipidic microparticles proteins, such as antibodies, or fragments thereof, conjugated to linkers significantly smaller than the protein. In view of the hydrophilic nature of antibodies and other proteins, the art has taught that the larger, protein portion of such a conjugate prevents the hydrophobic linking moiety from stable association with a lipidic microparticle.

SUMMARY OF THE INVENTION

The present invention provides a novel method of preparing cationic lipid:nucleic acid complexes that have increased shelf life. In one embodiment, these complexes are prepared by contacting a nucleic acid with an organic polycation, to produce a condensed or partially condensed nucleic acid. The condensed nucleic acid is then combined with an amphiphilic cationic lipid plus a neutral helper lipid such as cholesterol in a molar ratio from about 2:1 to about 1:2, producing the lipid:nucleic acid complex. Optionally, a hydrophilic polymer is subsequently added to the lipid:nucleic acid complex. Alternatively, the hydrophilic polymer is added to a lipid:nucleic acid complex comprising nucleic acid that has not been not condensed. These lipid:nucleic acid complexes have an increased shelf life, e.g., when stored at 22° C. or below, as compared to an identical lipid:nucleic acid complex in which the nucleic acid component has not been contacted with the organic polycation and/or in which the lipid:nucleic acid complex has not been contacted with a hydrophilic polymer.

In a particularly preferred embodiment, the polycation is a polyamine, more preferably a polyamine such as spermidine or spermine.

In another preferred embodiment, the lipid:nucleic acid complexes are prepared by combining a nucleic acid with an amphiphilic cationic lipid and then combining the complex thus formed with a hydrophilic polymer. This lipid:nucleic acid complex has an increased shelf life, e.g., when stored at 22° C. or below as compared to an identical complex that has not been combined with the hydrophilic polymer.

In one embodiment, the hydrophilic polymer is selected from the group consisting of polyethylene glycol (PEG), polyethylene glycol derivatized with phosphatidyl ethanolamine (PEG-PE), polyethylene glycol derivatized with tween, polyethylene glycol derivatized with distearoylphosphatidylethanolamine (PEG-DSPE), ganglioside $G_{M1}$ and synthetic polymers.

In one embodiment, the lipid:nucleic acid complex is lyophilized.

In any of the methods and compositions of this invention, the nucleic acid can be virtually any nucleic acid, e.g., a deoxyribonucleic acid (DNA) or a ribonucleic acid (RNA), and peptide nucleic acid (PNA) etc., and is most preferably a DNA. In a particularly preferred embodiment, the DNA is an expression cassette capable of expressing a polypeptide in a cell transfected with the lipid:nucleic acid complex.

In one embodiment the lipid:nucleic acid complexes are formed by first forming a liposome, and then combining the formed liposome with condensed or partially condensed nucleic acid to form a lipid:nucleic acid complex. Optionally, the lipid:nucleic acid complex is subsequently contacted with a hydrophilic polymer. The liposomes can alternatively be combined with an uncondensed nucleic acid to form a lipid:nucleic acid complex to which a hydrophilic polymer (e.g., PEG-PE) is later added. A lipid:nucleic acid complex prepared by the combination of nucleic acid and a liposome contacted with a hydrophilic polymer can be subsequently combined with additional hydrophilic polymer. In a preferred embodiment, the lipid and nucleic acid are combined in a ratio ranging from about 1 to about 20, more preferably from about 4 to about 16, and most preferably from about 8 to about 12 nmole lipid:µg nucleic acid. The lipid and hydrophilic polymer are combined in a molar ratio ranging from about 0.1 to about 10%, more preferably from about 0.3 to about 5% and most preferably from about 0.5% to about 2.0% (molar ratio of hydrophilic polymer to cationic lipid of the complex).

It will be appreciated that a targeting moiety (e.g., an antibody or an antibody fragment) can be attached to the lipid and/or liposome before or after formation of the lipid:nucleic acid complex. In a preferred embodiment, the targeting moiety is coupled to the hydrophilic polymer (e.g., PEG), where the targeting moiety/hydrophilic polymer is subsequently added to the lipid:nucleic acid complex. This provides a convenient means for modifying the targeting specificity of an otherwise generic lipid:nucleic acid complex.

In a particularly preferred embodiment, the method of increasing the shelf life of the lipid:nucleic acid complex includes the steps of combining an expression cassette with spermidine or spermine with an amphiphilic cationic lipid plus a helper lipid such as cholesterol, and a Fab' fragment of an antibody attached to a spacer, e.g., polyethylene glycol, so that the complex has increased shelf life when stored at about 4° C.

In one particularly preferred embodiment, the method of increasing the shelf life of the lipid:nucleic acid complex includes the steps of combining an expression cassette with spermidine or spermine with an amphiphilic cationic lipid, and a Fab' fragment of an antibody attached to a polyethylene glycol derivative. In another particularly preferred embodiment, includes the steps of combining an expression cassette with an amphiphilic cationic lipid, and a Fab' fragment of an antibody attached to a polyethylene glycol derivative so that the complex has increased shelf life when stored at about 4° C.

This invention also provides for a method of transfecting a nucleic acid into a mammalian cell, the method comprising contacting the cell with any one of the lipid:nucleic acid complexes prepared as described above. In one embodiment, the method uses systemic administration of a lipid:nucleic acid complex into a mammal. In a preferred embodiment, the method of transfecting uses intravenous administration of the lipid:nucleic acid complex into a mammal. In a particularly preferred embodiment, the method comprises contacting a specific cell that expresses a ligand that recognizes the Fab' fragment.

In yet another embodiment, this invention also provides for pharmaceutical composition comprising the lipid:condensed nucleic acid complex described above. The pharmaceutical compositions comprise a therapeutically effective dose of the lipid:nucleic acid complex and a pharmaceutically acceptable carrier or excipient.

In yet another embodiment, the invention also provides a kit for preparing a lipid:nucleic acid complex, the kit comprising a container with a liposome; a container with a nucleic acid; and a container with a hydrophilic polymer, wherein the liposome and the nucleic acid are mixed to form the lipid:nucleic acid complex and wherein the lipid:nucleic acid complex is contacted with the hydrophilic polymer. In a preferred embodiment, the hydrophilic polymer is derivatized with a targeting moiety, preferably an Fab' fragment. In another preferred embodiment, the nucleic acid is condensed.

This invention also provides for a lipid:condensed nucleic acid complex prepared using the method of increasing shelf life using nucleic acid condensed with an organic polycation, as summarized above.

The invention further provides a method for making lipidic microparticles bearing attached proteins. The method employs proteins which have been conjugated to linker molecules which will stably associate with lipidic microparticles. The invention therefore permits the attachment of proteins to the surface, for example, of lipidic microparticles which have been preformed.

BRIEF DESCRIPTION OF THE DRAWINGS

FIG. 1A illustrates cell transfection. SKBR-3 cells were plated at 50,000 cells per well in twelve-well plates and incubated overnight. Each well received 1 μg of P-CMWIVSLuc+plasmid which was complexed with liposomes at 5 nmole of DDAB. Cells were harvested after 24 hr incubation with complexes at 37° C. Values presented are mean from 2 wells. Values ranged within 10–30% of mean. FIG. 1B illustrates in vivo transfection in mice. Mice received via tail vein injection 40 μg of P-CMVIVS-Luc+plasmid, which was complexed with liposomes at 8 nmole DDAB per μg DNA ratio. Values presented are mean from 2 mice. Values ranged within 20–25% of mean.

DEFINITIONS

Figure 1A:
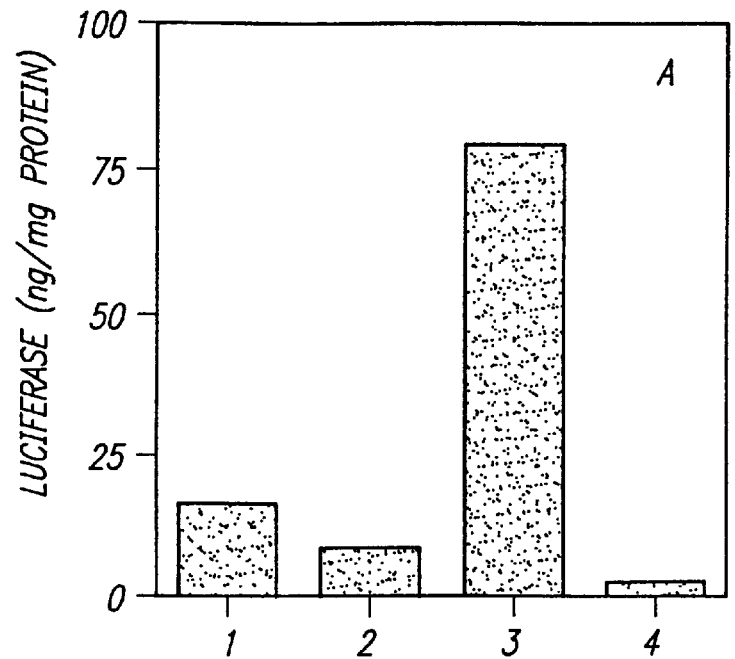
FIGS. 1A and 1B illustrate the role of neutral lipid in gene delivery. Three liposome formulations were tested for gene delivery to both culture cells (SKBR-3, human breast cancer cell) and mice (CD1, female, 20–25 g). Samples were: (1) DDAB/Chol (1:1); (2) DDAB/Chol/DOPE (1:0.5:0.5); (3) DDAB/DOPE (1:1); and (4) DDAB alone.

The following abbreviations are used herein: Chol, cholesterol; PA, phosphatidic acid; PC, phosphatidylcholine; PI, phosphatidylinositol; SM, sphinogmyelin; M-DPE, maleimide derivatized dipalmityolethanolamine; PBS, phosphate buffered saline; LUV, large unilamellar vesicles; MLV, multilamellar vesicles; PE, phosphatidylethanolamine; PEG, polyethylene glycol; PEG-PE, polyethylene glycol derivatized phosphatidylethanolamine, DC-chol, 3β [N-(N', N'-dimethylaminoethane) carbanoyl]-cholesterol; DDAB, Dimethyidioctadecylammonium bromide; DMEPC, Dimyristoylglycero-3-ethyl phosphocholine; DODAP, Dioleoyl-3-dimethylamm onium propane; DOEPC, Dioleoylglycero-3-ethyl phosphocholine; DOGS, N,N-Dioctadecylamidoglycyl spermine; DOPE, Dioleoylphosphatidylethanolamine; DOTAP, Dioleoyl-3-trimethylammonium propane; DOTMA, N-[2,3-(dioleyloxy) propyl]-N,N,N-trimethyl ammonium bromide; DSPE, Distearoylphosphatidylethanolamine; PEG-PE, N-[ω-methoxypoly(oxyethylene)-aoxycarbonyl]-DSPE; POEPC, Pahmitoyloleoylglycero-3-ethyl phosphocholine.

The term "amphiphilic cationic lipid" is intended to include any amphiphilic lipid, including synthetic lipids and lipid analogs, having hydrophobic and polar head group moieties, a net positive charge, and which by itself can form spontaneously into bilayer vesicles or micelles in water, as exemplified by phospholipids. The term also includes any amphiphilic lipid that is stably incorporated into lipid bilayers in combination with phospholipids with its hydrophobic moiety in contact with the interior, hydrophobic region of the bilayer membrane, and its polar head group moiety oriented toward the exterior, polar surface of the membrane.

The term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The terms "ligand" or "targeting moiety", as used herein, refer generally to all molecules capable of specifically binding to a particular target molecule and forming a bound complex as described above. Thus the ligand and its corresponding target molecule form a specific binding pair. Examples include, but are not limited to antibodies, lymphokines, cytokines, receptor proteins such as CD4 and CD8, solubilized receptor proteins such as soluble CD4, hormones, growth factors, and the like which specifically bind desired target cells, and nucleic acids which bind corresponding nucleic acids through base pair complementarity. Particularly preferred targeting moieties include antibodies and antibody fragments (e.g., the Fab' fragment).

The term "lipid:nucleic acid complex" refers to the product made by mixing amphiphilic cationic lipids or liposomes with a nucleic acid. The term "CLDC," which stands for "cationic lipid:DNA complex" as used herein is not limited to DNA and is a convenient abbreviation for lipid:nucleic acid complex. The lipid:nucleic acid complex can also include a helper lipid. The helper lipid is often a neutral lipid such as DOPE or cholesterol with cholesterol being most preferred. The lipid:nucleic acid complex may also contain other compounds such as a polycation that are in contact with the nucleic acid of the complex, producing condensed nucleic acid, and hydrophilic polymers such as PEG and derivatized PEG.

The terms "immunoliposome" and "immunolipid:nucleic acid complex" refer to a liposome or lipid:nucleic acid complex bearing an antibody or antibody fragment that acts as a targeting moiety enabling the lipid:nucleic acid complex to specifically bind to a particular "target" molecule that may exist in solution or may be bound to the surface of a cell. Where the target molecule is one that is typically found in relative excess (e.g., ≧10-fold) and in association with a particular cell type or alternatively in a multiplicity of cell types all expressing a particular physiological condition the target molecule is said to be a "characteristic marker" of that cell type or that physiological condition. Thus, for example, a cancer may be characterized by the overexpression of a particular marker such as the HER2 (c-erbB-21neu) proto-oncogene in the case of breast cancer.

A "hydrophilic polymer" as used herein refers to highly hydrated flexible neutral polymers attached to lipid molecules. Examples include, but are not limited to polyethylene glycol (PEG), polyethylene glycol derivatized with phosphatidyl ethanolamine (PEG-PE), polyethylene glycol derivatized with tween, polyethylene glycol derivatized with distearoylphosphatidylethanolamine (PEG-DSPE), ganglioside GMI and synthetic polymers. Such polymers typically have a molecular weight in the range of 1000–10,000. Preferably, the molecular weight for PEG is approximately 2000.

"Transfection" refers to contacting a living cell with a nucleic acid, for example, as part of a lipid:nucleic acid complex.

"Transfection activity" refers to the efficiency of introducing a nucleic acid into a living cell. Transfection efficiency may be measured by determining the amount of expression of a reporter gene that has been transfected into the cell as part of a lipid:nucleic acid complex, for example, by fluorescent or functional assays.

The terms "condensed nucleic acid" and "partially condensed nucleic acid" are used to refer to a nucleic acid that has been contacted with an organic cation for example, polyamines, including spermine and spermidine, polyammonium molecules such as Polybrene (hexadimethrine bromide), basic polyamino acids, and basic proteins. Condensed nucleic acids typically occupy a significantly smaller volume than non-condensed nucleic acids. It is recognized, however, that the degree of condensation may vary with local environment (e.g., lipid as opposed to aqueous environment).

The term "shelf life" when used to refer to the lipid:nucleic acids disclosed herein refers to the period of time the lipid:nucleic acid complex can be stored (under defined conditions e.g., at 4° C.) before losing its biological activity. The biological activity assayed for determination of shelf life in the present invention is the ability of the lipid:nucleic acid complex to transfect mammalian cells in vivo after intravenous administration. The "shelf life" of a lipid:nucleic acid complex is conveniently determined by assaying by gene expression from reporter nucleic acids in the lipid:nucleic acid complex as described herein.

An "expression cassette" refers to a promoter operably linked to a DNA molecule, containing all the elements required for expression of that DNA molecule in a living cell. The expression cassette may contain additional elements such as enhancers, replication origins and the like, forming an expression vector. "Organic polycation" or "polycation" refer to a an organic polymeric structure where more than one unit of the polymer bears a negative charge and the net charge of the polymer is positive. Examples of such an organic cation are polyamines, including spermine and spermidine, polyammonium molecules such as Polybrene (hexadimethrine bromide), basic polyamino acids, or basic proteins.

A "pharmaceutically acceptable carrier" is a material that is not biologically or otherwise undesirable, i.e., the material can be administer to an individual along with the lipid:nucleic acid complex without causing unacceptable biological effects or interacting in a deleterious manner with any of the other components of the pharmaceutical composition in which it is contained.

The term "nucleic acid" refers to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like.

The term "mole percent" when referring to the percentage of hydrophilic polymer in a liposome is expressed relative to the cationic lipid in the liposome unless otherwise stated. Thus, for example, in a liposome comprising a ratio of DDAB to cholesterol (Chol) of 100:100, a 4 mole percent of hydrophilic polymer (e.g., PEG) would represent a ratio of DDAB:Chol:PEG of about 100:100:4.

The term "identical" refers to a composition that is formed using the same compounds as another composition, where the compositions do not differ in a statistically significant manner.

The term "systemic administration" refers to a method of administering a compound or composition to a mammal so that the compound or composition is delivered to many sites in the body via the circulatory system.

As used herein, "linker molecule" means a molecule comprising (a) a hydrophobic domain, (b) a hydrophilic polymer chain terminally attached to the hydrophobic domain, and (c) a chemical group reactive to one or more functional groups on a protein molecule and attached to the said polymer chain at, or near to, the terminus contralateral to the hydrophobic domain.

The term "hydrophobic domain" of, for example, a linker molecule, means a fatty acid, fatty alcohol, sterol, or other hydrophobic molecule capable of distribution into a lipid phase from an aqueous medium. For example, a hydrophobic domain may be a diacylglycerol, a phospholipid, a sterol, such as cholesterol, or a diacylamide derivative, such as N,N-distearoyl-glycineamide.

The term "lipid moiety" with reference to a protein molecule means an array composed of one or more hydrophobic domains directly covalently bound to the protein molecule.

The terms "protein" and "peptide" are generally differentiated in the art by molecular weight, with polypeptides below 6,000 Daltons being considered peptides and those at or above 6,000 Daltons being considered proteins. See, e.g., McMurray, *Organic Chemistry* (Brooks/Cole Publishing Co., Belmont, Calif.)(1988), at p. 971. The use of these terms herein follows this distinction.

DETAILED DESCRIPTION

This invention provides methods of increasing the shelf life of cationic lipid:nucleic acid complexes, and in vivo and/or in vitro transfection efficiency of these complexes. Such complexes have attracted considerable interest as a means of delivering nucleic acids expressing various therapeutic polypeptides as a means of delivering therapeutic (e.g., antisense) nucleic acids themselves. Unfortunately, it has been difficult to maintain and store homogeneous lipid-:nucleic acid complexes suitable for in vivo administration. The complexes tend to aggregate rapidly or decompose within a relatively short time. This instability has required use of these complexes within a short period of time after preparation, often as little as 30 minutes up to a few hours. Thus, for example, in recent clinical trials using cationic lipids as a carrier for DNA delivery, the DNA and lipid components were mixed at the bedside and used immediately (Gao et al., *Gene Therapy* 2: 710–722 (1995)).

This lipid:nucleic acid complex instability provides a significant hindrance to the widespread acceptance of cationic lipid:nucleic acid complexes as therapeutics. The necessity of preparation of the complex shortly before use requires that a pharmaceutical facility be in relatively close proximity to the area of use. Alternatively, combination of the lipid and nucleic acid at the bedside imposes a substantial labor burden, introduces quality control problems in insuring adequate complexation, and creates a source of potential error.

The present invention solves these problems by providing methods of significantly increasing the shelf (storage) life of lipid:nucleic acid complexes. The methods generally involve: (1) condensing the nucleic acid before incorporation into the lipid:nucleic acid complex; (2) combining a lipid:nucleic acid complex with a hydrophilic polymer (e.g., PEG); and (3) both condensing the nucleic acid prior to complex formation and combining the complex with a hydrophilic polymer.

While condensation of nucleic acids may lead to stability of the nucleic acid in isolation (e.g., in an aqueous buffer), it was a surprising discovery of this invention that the use of a condensing agent (e.g., an organic polycation) provides a lipid:nucleic acid complex that remains capable of transfecting a cell in vivo even after a period of prolonged storage (e.g., cold storage at a temperature of about 22° C. or below, more preferably ranging from about 0° C. to about 22° C., and most preferably at about 4° C.).

It was also a surprising discovery that lipid:nucleic acid complexes combined with a hydrophilic polymer attached to an amphipathic lipid (e.g., PEG-PE) also show an increased shelf life. Without being bound by a particular theory, it is believed that when the cationic lipid:DNA complex ("CLDC") is contacted with the hydrophilic polymer, the hydrophilic polymer locates and is incorporated into hydrophobic pockets in the complex via its hydrophobic side chains, while leaving the hydrophilic part at the exterior surface, thereby stabilizing the entire complex.

In view of these discoveries, this invention provides methods of increasing the shelf life of cationic lipid:nucleic acid complexes. The methods generally involve either condensing the nucleic acid using a polycation and/or contacting, e.g., coating, the lipid:nucleic acid complex with a hydrophilic polymer. This invention also include the lipid:nucleic acid complexes thus prepared.

This invention further provides methods for forming lipidic microparticles with attached proteins suitable, for example, for targeting the microparticles to selected cells or tissues. The methods provide a number of advantages over prior art methods:

(1) due to the quantitative nature of insertion, the number of proteins per particle is highly reproducible and can be precisely defined;

(2) more than one kind of protein can be attached to the surface of the same particle, in a precise proportion;

(3) if the protein-linker conjugate is purified before insertion into a particle surface, the particle will not bear unconjugated linkers;

(4) the particle may contain, in its composition, molecules reactive with the linker active group. For example, the particle may contain thiols, even if the active group is maleimide;

(5) if the particle is a vesicle, the linker/protein molecules will only be present on the outer surface; and, (6) the method increases the utility of premade, known particles, such as commercially made pharmaceutical liposomes, by permitting the addition of surface-attached conjugates bearing proteins of interest.

I. Cationic lipid:nucleic acid complexes

As explained above, this invention provides methods of increasing the storage life (shelf life) of lipid:nucleic acid complexes. In a preferred embodiment the complexes are formed by combination of a nucleic acid with a liposome. It is recognized, however, that the lipids need not be provided as a liposome. It is also recognized that after complexation, the lipid:nucleic acid complex may no longer exist as a true vesicle and therefore is not generally regarded as a liposome. The preparation of lipid:nucleic acid complexes is well known to one of skill in the art (see, e.g., reviewed in Crystal, *Science* 270: 404–410 (1995); Blaese et al., *Cancer Gene Ther.* 2: 291–297 10 (1995); Behr et al., *Bioconjugate Chem.* 5: 382–389 (1994); Remy et al., *Bioconjugate Chem.* 5: 647–654 (1994); and Gao et al., *Gene Therapy* 2: 710–722 (1995)). The various components and construction of the stabilized lipid:nucleic acid complexes of the invention are described in detail below.

A. Amphiphilic cationic lipids

As indicated above, the methods of this invention involve complexing a cationic lipid with a nucleic acid. The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

The cationic lipid can be used alone, or in combination with a "helper" lipid. Preferred helper lipids are non-ionic or uncharged at physiological pH. Particularly preferred nonionic lipids include, but are not limited to cholesterol and DOPE, with cholesterol being most preferred.

The molar ratio of cationic lipid to helper can range from 2:1 to about 1:2, more preferably from about 1.5:1 to about 1:1.5 and most preferably is about 1:1. Additional cationic and nonionic lipids suitable for use in the lipid:nucleic acid complexes of the present invention are well known to persons of skill in the art and are cited in a variety of well known sources, e.g., *McCutcheon's Detergents and Emulsifiers and McCutcheon's Functional Materials,* Allured Publishing Co., Ridgewood, N.J. Preferred lipids include DDAB:cholesterol or DOTAP:cholesterol at a molar ratio of 1:1.

B. Nucleic acid

The lipid:nucleic acid complexes contain a nucleic acid, typically an expression cassette that is constructed using recombinant techniques. A recombinant nucleic acid is prepared by first isolating the nucleic acid of interest. The isolated nucleic acid is then ligated into a cassette or vector suitable for expression of the gene. Methods for preparing a recombinant nucleic acid are known by those skilled in the art (see Sambrook et al., *Molecular Cloning: A Laboratory Manual* (2d ed. 1989)).

The gene of interest, for example, a gene encoding a therapeutic polypeptide, or a reporter gene, can be inserted into an "expression vector," "cloning vector," or "vector," terms which usually refer to plasmids or other nucleic acid molecules that are able to replicate in a chosen host cell and express the gene of interest. Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers and enhancers. Selectable markers, e.g., tetracycline resistance or hygromycin resistance, permit detection and/or selection of those cells transformed with the desired DNA sequences (see, e.g., U.S. Pat. No. 4,704,362). The particular vector used to transport the genetic information into the cell is also not particularly critical. Any of the conventional vectors used for expression of recombinant proteins in prokaryotic or eukaryotic cells can be used.

The expression vectors typically have a transcription unit or expression cassette that contains all the elements required for the expression of the nucleic acid in the host cells. A typical expression cassette contains a promoter operably linked to the DNA sequence encoding a protein. The promoter is preferably positioned about the same distance from the heterologous transcription start site as it is from the transcription start site in its natural setting. As is known in the art, however, some variation in this distance can be accommodated without loss of promoter function.

In the expression cassette, the nucleic acid sequence of interest can be linked to a sequence encoding a cleavable signal peptide sequence to promote secretion of the encoded protein by the transformed cell. The expression cassette should also contain a transcription termination region downstream of the structural gene to provide for efficient termination. The termination region can be obtained from the same gene as the promoter sequence or can be obtained from a different gene.

For more efficient translation in mammalian cells of the mRNA encoded by the structural gene, polyadenylation sequences are also commonly added to the expression cassette. Termination and polyadenylation signals that are suitable for the present invention include those derived from SV40, or a partial genomic copy of a gene already resident on the expression vector.

In addition to the expression cassette, many expression vectors optimally include enhancer elements that can stimulate transcription up to 1,000 fold from linked homologous or heterologous promoters. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long terminal repeat from various retroviruses such as murine leukemia virus, murine or Rous sarcoma virus, and HIV (see *Enhancers and Eukaryotic Expression* (1983)).

In addition to the recombinant nucleic acids discussed above, synthetic nucleic acids or oligonucleotides can also be used in the invention. As a general point regarding the nucleic acids used in the invention, those of skill in the art recognize that the nucleic acids used in the invention include both DNA and RNA molecules, as well as synthetic, non-naturally occurring analogs of the same, and heteropolymers, of deoxyribonucleotides, ribonucleotides, and/or analogues of either. The particular composition of a nucleic acid or nucleic acid analogue will depend upon the purpose for which the material will be used and the environment in which the material will be placed. Modified or synthetic, non-naturally occurring nucleotides have been designed to serve a variety of purposes and to remain stable in a variety of environments, such as those in which nucleases are present, as is well known in the art. Modified or synthetic non-naturally occurring nucleotides, as compared to naturally occurring ribo- or deoxyribonucleotides may differ with respect to the carbohydrate (sugar), phosphate bond, or base portions of the nucleotide, or may even contain a non-nucleotide base (or no base at all) in some cases (see, e.g., Arnold et al., PCT patent publication no. WO 89/02439). For example, the modified or non-naturally occurring nucleic acids of the invention can include biotinylated nucleic acids, O-methylated nucleic acids, methylphosphonate backbone nucleic acids, phosphorothioate backbone nucleic acids, or polyamide nucleic acids.

Oligonucleotides, such as antisense RNA described below, preferably are synthesized on an Applied BioSystems or other commercially available oligonucleotide synthesizer according to specifications provided by the manufacturer. Oligonucleotides may be prepared using any suitable method, such as the phosphotriester and phosphodiester methods, or automated embodiments thereof. In one such automated embodiment, diethylphosphoramidites are used as starting materials and may be synthesized as described by Beaucage et al., *Tetrahedron Letters* 22: 1859 (1981), and U.S. Pat. No. 4,458,066.

C. Condensed nucleic acid

Small polycationic molecules are known to condense nucleic acids via electrostatic charge-charge interactions (Plum et al., *Biopolymers* 30: 631–643 (1990)). The pretreatment of nucleic acid with polyamines can therefore reduce the number of charge sites for complexing with cationic liposomes. However, condensing nucleic acid prior to lipid complex formation produced the surprising result of increased shelf life for lipid:nucleic acid complexes, as measured by transfection efficiency. The lipid:nucleic acid complexes formed with such pretreatment were stable at a lower ratio of lipid to DNA without aggregation. Organic polycations such as polyamines, polyammonium molecules, and basic polyamino acids, and their derivatives are used to condense the nucleic acid prior to lipid complex formation. A preferred embodiment uses polyamines such as spermidine and spermine to condense the nucleic acid (see, e.g., Example 1).

D. Hydrophilic polymer

It has been established recently that PEG-PE incorporation in liposomes produces steric stabilization resulting in longer circulation times in blood (Allen et al., *Biochim. Biophys. Acta* 1066: 29–36 (1991); Papahadjopoulos et al., *Proc. Natl. Acad. Sci. USA* 88: 11460–11464 (1991)). In the present invention, inserting PEG-PE (e.g., 1% of total lipid) into the freshly formed lipid:nucleic acid complexes prevents the complexes from aggregating during storage. It was a surprising discovery, however, that the incorporation of PEG-PE did not inhibit transfection activity in vivo and also that the in vitro transfection activity, which was inhibited, was regained by the incorporation of Fab' fragment conjugated at the end of the PEG-PE. The presence of hydrophilic polymers in the lipid:nucleic acid complex provides increased shelf life, as measured by transfection efficiency after storage. Thus, it is desirable to add a hydrophilic polymer such as polyethylene glycol (PEG)-modified lipids or ganglioside $G_{M1}$ to the liposomes. PEG may also be derivatized with other amphipathic molecules such as fatty acids, sphingolipids, glycolipids, and cholesterol. Addition of such components prevents liposome aggregation during coupling of the targeting moiety to the liposome. These components also provide a means for increasing circulation lifetime of the lipid:nucleic acid complexes.

A number of different methods may be used for the preparation of PEG for incorporation into liposomes. In one preferred embodiment, PEG is incorporated as PEG derivatized phosphatidylethanolamine (PEG-PE) or PEG derivatized distearoyl phosphatidylethanolamine (PEG-DSPE). Methods of preparing PEG-PE are well known and typically involve using an activated methoxy PEG (with only one reactive end) and PE. Thus PEG-succinimidyl succinate may be reacted in a basic organic solvent (Klibanov et al., *FEBS Lett.* 268: 235–237 (1990)). A particularly preferred method of PEG-PE preparation is based on reaction of the PEG with carbonyldiimidazole followed by addition of PE (see Woodle et al., *Proc. Intern. Symp. Control. Rel. Bioact. Mater.* 17: 77–78 (1990); Papahadjopoulos et al.,*Proc. Natl. Acad. Sci. USA* 88: 11460–11464 (1991); Allen et al., *Biochim. Biophys. Acta.* 1066: 29–36 (1991); Woodle et al., *Biochim. Biophys. Acta* 1105: 193–200 (1992); and Woodle et al.,*Period. Biol.* 93: 349–352 (1991)). Similarly, cyanuric chloride activated PEG in a basic organic solvent is described by Blume et al., *Biochim. Biophys. Acta.* 1029: 91–97 (1990) and U.S. Pat. No. 5,213,804. A completely different approach is based on coupling the PEG with preformed liposomes utilizing tresyl chloride activated PEG which is then added to liposomes containing PE at high pH (Senior et al., *Biochim. Biophys. Acta.* 1062: 77–82 (1991)). Derivatized PEG is also commercially available. Thus, for example, PEG-PE is available from Avanti Polar lipids (Alabaster, Ala.). One of skill in the art will recognize that many other linkages are available, e.g., PEG linked detergents such as tweens and insertion of PEG derivatized lipid into formed lipid:nucleic acid complexes.

E. Fab' antibody fragment

In a preferred embodiment, the lipid:nucleic acid complexes of the present invention are conjugated to the Fab' fragment of an antibody, which acts as a targeting moiety enabling the lipid:nucleic acid complex to specifically bind a target cell bearing the target molecule (e.g., characteristic marker) to which the Fab' antibody fragment is directed. Smaller peptides from the hypervariable region or from another peptide interacting with a specific cell surface ligand may also be conjugated to the complexes. In general terms, the Fab' fragment of an antibody represents a monomer comprising the variable regions and the $C_H1$ region of one arm of an antibody. One such preferred embodiment is described in Example 2.

An "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. In particular, pepsin digests an antibody below the disulfide linkages in the hinge region to produce F(ab)'$_2$, a dimer of Fab' which itself is a light chain joined to $V_H$-$C_H1$ by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see Fundamental Immunology, W. E. Paul, ed., Raven Press, N.Y. (1993) for more antibody fragment terminology). While the Fab' fragment is defined in terms of the digestion of an intact antibody, one of skill will appreciate that such Fab' fragments may be synthesized de novo either chemically or by utilizing recombinant DNA methodology.

The Fab' fragments used in the present invention may be derived from antibodies of animal (especially mouse or rat) or human origin or may be chimeric (Morrison et al., *Proc Natl. Acad. Sci. USA* 81: 6851–6855 (1984)) or humanized (Jones et al., *Nature* 321: 522–525 (1986), and published UK patent application No. 8707252).

The Fab' fragment is selected to specifically bind to a molecule or marker characteristic of the surface of the cells to which it is desired to deliver the contents of the cationic lipid:nucleic acid complex. A molecule is characteristic of cell, tissue, or physiological state when that molecule is typically found in association with that cell type or alternatively in a multiplicity of cell types all expressing a particular physiological condition (e.g., transformation). A specific characteristic marker is preferably found on the surfaces of cells of a particular tissue or cell type or on the surfaces of tissues or cells expressing a particular physiological condition and on no other tissue or cell type in the organism. One of skill will recognize however, that such a level of specificity of the marker is often not required. For example a characteristic cell surface marker will show sufficient tissue specificity if the only non-target tissues are not accessible to the lipid:nucleic acid complex. Alternatively, effective specificity may be achieved by overexpression of the marker in the target tissue as compared to other tissues. This will result in preferential uptake by the target tissue leading to effective tissue specificity. Thus for example, many cancers are characterized by the overexpression of cell surface markers such as the HER2 (c-erbB-2, neu) proto-oncogene encoded receptor in the case of breast cancer.

One of skill will recognize that there are numerous cell surface markers that provide good characteristic markers depending on the particular tissue it is desired to target. These cell surface markers include, but are not limited to carbohydrates, proteins, glycoproteins, MHC complexes, interleukins, and receptor proteins such as HER, CD4 and CD8 receptor proteins as well as other growth factor and hormone receptor proteins.

Growth factor receptors are particularly preferred characteristic cell surface markers. Growth factor receptors are cell surface receptors that specifically bind growth factors and thereby mediate a cellular response characteristic of the particular growth factor. The term "growth factor", as used herein, refers to a protein or polypeptide ligand that activates or stimulates cell division or differentiation or stimulates biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin, interleukin 13 receptor (IL13R), and the like. One of skill in the art recognizes that the term growth factor as used herein generally includes cytokines and colony stimulating factors.

Particularly preferred markers are found in the HER family of growth factor receptors. More specifically HER1, HER2, HER3 and HER4 are more preferred with HER2 most preferred. The HER receptors comprise protein tyrosine kinases that themselves provide highly specific antibody targets. Thus, in one embodiment, the P185 tyrosine kinase of HER2 provides a most preferred target for the Fab' fragment of the utilized in the immunolipid:nucleic acid complexes of the present invention.

It will be appreciated that the characteristic marker need not be a naturally occurring marker, but rather may be introduced to the particular target cell. This may be accomplished by directly tagging a cell or tissue with a particular marker (e.g., by directly injecting the particular target tissue with a marker, or alternatively, by administering to the entire organism a marker that is selectively incorporated by the target tissue. In one embodiment, the marker may be a gene product that is encoded by a nucleic acid in an expression cassette. The marker gene may be under the control of a promoter that is active only in the particular target cells. Thus introduction of a vector containing the expression cassette will result in expression of the marker in only the particular target cells. One of skill in the art will recognize that there are numerous approaches utilizing recombinant DNA methodology to introduce characteristic markers into target cells.

In one preferred embodiment, the targeting moiety will specifically bind products or components of a growth factor receptor, in particular products of the HER2 (c-erbB-2, neu) proto-oncogene. It is particularly preferred that the targeting moiety bind the growth factor receptor-tyrosine kinase encoded by HER2, protein p185$^{HER2}$, which is commonly overexpressed in breast cancers (Slamon et al., *Science* 235: 177–182 (1987). Other suitable targets for the targeting moiety include, but are not limited to EGFR (HER1), HER3, and HER4, combinations of these receptors, and other markers associated with cancers. Other antibodies of interest include, but are not limited to BR96 (Friedman et al., *Cancer Res.* 53: 334–339 (1993), e23 to erbB2 (Batra et al, *Proc. Natl. Acad. Sci. USA* 89: 5867–5871 (1992)), PR1 in prostate cancer (Brinklann et al., *Proc. Natl. Acad. Sci. USA*. 90: 547–551 (1993)), and K1 in ovarian cancer (Chang et al. *Int. J. Cancer* 50: 373–381 (1992).

Immunolipid:nucleic acid complexes of the present invention may be prepared by incorporating the Fab' fragment into the liposomes or lipids by a variety of techniques well known to those of skill in the art. The Fab' is added to the lipid:nucleic acid complex either before or after complex formation. For example, a biotin conjugated Fab' may be bound to a liposome containing a streptavidin. Alternatively, the biotinylated Fab' may be conjugated to a biotin derivatized liposome by an avidin or streptavidin linker. Thus, for example, a biotinylated monoclonal antibody was biotinylated and attached to liposomes containing biotinylated phosphatidylethanolamine by means of an avidin linker (see, e.g., Ahmad et al., *Cancer Res.* 52: 4817–4820 (1992)). Typically about 30 to 125 and more typically about 50 to 100 Fab' fragments per lipid:nucleic acid complex are used.

In a preferred embodiment, the targeting moiety may be directly conjugated to the liposome. Such means of direct conjugation are well known to those of skill in the art (see, e.g., Gregoriadis, *Liposome Technology* (1984) and Lasic, *Liposomes: from Physics to Applications* (1993)). Particularly preferred is conjugation through a thioether linkage. This may be accomplished by reacting the antibody with a maleimide derivatized lipid such as maleimide derivatized phosphatidylethanolamine (M-PE) or dipalmitoylethanolamine (M-DEP). This approach is described in detail by Martin et al. *J. Biol. Chem.* 257: 286–288 (1982).

II. Preparation of liposomes

A variety of methods are available for preparing liposomes as described in, e.g., Szoka et al., *Ann. Rev. Biophys. Bioeng.* 9:467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, *Proc. Natl. Acad. Sci. USA* 75: 4194–4198 (1978); Deamer & Bangham, *Biochim. Biophys. Acta* 443: 629–634 (1976); Fraley et al., *Proc. Natl. Acad. Sci. USA* 76: 3348–3352 (1979); Hope et al., *Biochim. Biophys. Acta* 812: 55–65 (1985); Mayer et al., *Biochim. Biophys. Acta* 858: 161–168 (1986); Williams et al., *Proc. Natl. Acad. Sci. USA* 85: 242–246 (1988), Liposomes, ch. 1

(Ostro, ed., 1983); and Hope et al., *Chem. Phys. Lip.* 40: 89 (1986). Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

In a preferred embodiment, mostly unilammellar liposomes are produced by the reverse phase evaporation method of Szoka & Papahadjopoulos, *Proc. Natl. Acad. Sci. USA*, 75: 4194–4198 (1978).

Unilamellar vesicles are generally prepared by sonication or extrusion. Sonication is generally performed with a bath-type sonifier, such as a Branson tip sonifier at a controlled temperature as determined by the melting point of the lipid. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Following liposome preparation, the liposomes that have not been sized during formation may be sized by extrusion to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. Nos. 4,529,561 or 4,737,323. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10: 421–450 (1981). Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of about 0.05 microns to about 0.5 microns. More preferred are liposomes having a size of about 0.05 to 0.2 microns.

III. Formation of lipid:nucleic acid complexes

It was a discovery of this invention that stabilized lipid-:nucleic acid complexes (e.g., having condensed nucleic acid and/hydrophilic polymer) tended not to form visible large aggregates and had increased transfection efficiency and shelf life. Nucleic acid/liposome ratios for preparing lipid:nucleic acid complexes that do not form visible large aggregates can be determined by one of skill in the art. Typically, the ratio is determined by mixing fixed amounts of a nucleic acid, e.g., a plasmid, to various amounts of liposomes (see Example 1). In general, lipid:nucleic acid complexes are formed by pipetting the nucleic acid (e.g., plasmid DNA) into a liposome suspension of equal volume and mixing rapidly. Routinely, liposomes containing 5–15 nmole of a lipid such as DDAB or DOPE (as described above) form a complex with 1 $\mu$g plasmid, without forming visible large aggregates. Inspection for visible large aggregates is typically performed without the aid of a microscope. The endpoint of the titration of the amounts of lipid and nucleic acid is also achieved by assaying for increased transfection efficiency, either in vitro or in vivo, as compared to a non-stabilized control (as described below).

To keep the lipid:nucleic acid complexes from forming large aggregates and losing transfecting activity with time, two approaches are taken: (1) incorporating a small amount of a hydrophilic polymer such as PEG-PE (approx. 1% mole ratio) into lipid:nucleic acid complexes within a few minutes after their preparation; and/or (2) condensing the nucleic acid with a polycation such as a polyamine (e.g., approximately 0.05 to 5.0 nmole of spermidine per $\mu$g DNA) prior to mixing with the liposomes. The optimal amount of the polyamines and hydrophilic polymer can be determined by one of skill in the art by titrating the polyamine or hydrophilic polymer with the nucleic acid so that the formed complexes do not form large, e.g., visible, aggregates. The size of these lipid:nucleic acid complexes can be estimated by dynamic light scattering to be in the range of 410±150 nm. The endpoint of the titration is also achieved by assaying for increased transfection efficiency either in vitro or in vivo, as compared to a non-stabilized control (as described below).

IV. Transfection and gene therapy with lipid:nucleic acid complexes

The present invention provides lipid:nucleic acid complexes that have increased shelf life, for transfection of mammalian cells in vitro, in vivo, and ex vivo, and methods of production and transfection of such complexes. In particular, this invention relies in part on the unexpected discovery that a lipid:nucleic acid complex comprising nucleic acid that has been condensed by contact with an organic polycation demonstrates an increased shelf life. In addition, this invention relies on the unexpected discovery that a lipid:nucleic acid complex, which is mixed with a hydrophilic polymer after lipid:nucleic acid complex formation, exhibits high transfection activity and increased shelf life, as measured by transfection activity after storage. Such lipid:nucleic acid complexes having increased shelf life are useful, e.g., for in vitro and ex vivo transfection of cells, and for delivery of nucleic acids into cells for mammalian gene therapy in vivo and following intravenous administration.

Using lipid:nucleic acid complexes to deliver nucleic acids into different mammalian cell types results in a safe method of transfer, and high efficiency of gene transfer. Transfection of cells in vivo with lipid:nucleic acid complexes is known to those skilled in the art and can be performed using standard techniques, as discussed in Example 1 (see, e.g., Sambrook et al., *Molecular Cloning: A Laboratory Manual* (2d ed. 1989); Ausubel et al., *Current Protocols in Molecular Biology* (1995)).

Any heterologous nucleic acid that is suitable for introduction into a host cell can be used in the present invention by one skilled in the art. Genes useful for gene therapy can be introduced into mammals using the methods and vectors of this invention. Genes encoding blood proteins, enzymes, hormones, ribozymes, antisense RNA, viral inhibitors, and ion channel proteins are examples of heterologous nucleic acids useful in gene therapy. A functional heterologous gene can be used to replace a mutated gene in a mammal using gene therapy. For example, the gene encoding β-globin can be used to treat β-thalassemia; and the gene encoding CFTR can be used to treat cystic fibrosis. Genes encoding selectable markers, such as those that confer antibiotic resistance, can be used to detect and isolate cells transfected with the lipid:nucleic acid complex. Reporter genes such as luciferase, ,-galactosidase, chloramphenicol acetyl transferase (CAT), human growth hormone (hGH), and the green fluorescent protein (GFP) are preferred examples of genes that can be used in assays to determine transfection efficiency. In one embodiment of the invention, luciferase can be used as a reporter gene to determine transfection efficiency.

Transfection efficiency of a reporter gene can be determined with an assay that is appropriate for the reporter gene in use. Such assays are known to those skilled in the art. For example, the HGH reporter assay is immunologically based and employs commercially available radioimmunoassay kits. In a preferred embodiment of the invention, the luciferase assay is used to detect transfection and expression of the luciferase reporter gene. The luciferase assay is preferred because it is highly sensitive and does not use radioactivity. A luminometer can be used to measure the luciferase enzyme activity, as described in Example 1.

Gene therapy provides methods for combating chronic infectious diseases such as HIV infection, as well as non-infectious diseases such as cancer and birth defects (see generally Anderson, *Science* 256: 808–813 (1992); Yu et al., *Gene Ther.* 1: 13–26 (1994)). Gene therapy can be used to transduce cells with either an ex vivo or an in vivo procedure. Ex vivo methods for gene therapy involve transducing the cell outside of the mammal with a lipid:nucleic acid complex of this invention, and introducing the cell back into the organism. The cells can be hematopoietic stem cells isolated from bone marrow or other cells that can be transfected by lipid:nucleic acid complexes.

In humans, hematopoietic stem cells can be obtained from a variety of sources including cord blood, bone marrow, and mobilized peripheral blood. Purification of CD34+cells can be accomplished by antibody affinity procedures (see Ho et al., *Stem Cells* 13 (suppl. 3): 100–105 (1995); see also Brenner, *J. Hematotherapy* 2: 7–17 (1993)). Cells can also be isolated and cultured from patients. Alternatively, the cells used for ex vivo procedures can be those stored in a cell bank (e.g., a blood bank). The advantage to using stem cells is that they can be differentiated into other cell types in vitro, or can be introduced into a mammal (such as the donor of the cells) where they will engraft in the bone marrow. Methods for differentiating bone marrow cells in vitro into clinically important immune cell types using cytokines such as GM-CSF, IFN-γ and TNF-α are known (see, e.g., Inaba et al., *J. Exp. Med.* 176: 1693–1702 (1992)).

Delivery of a nucleic acid can also be achieved using in vivo gene therapy. The lipid:nucleic acid complexes of the invention can be administered directly to a patient, preferably a human. In vivo and ex vivo administration is by any of the routes normally used for introducing a molecule or cell into ultimate contact with blood or tissue cells. Lipid:nucleic acid complexes of the invention are administered in any suitable manner, preferably with pharmaceutically acceptable carriers.

Suitable methods of administering such non-viral particles in the context of the present invention to a patient are known to those skilled in the art. Preferably, the pharmaceutical compositions are administered using aerosol administration (e.g., using a nebulizer or other aerosolization device), and parenterally, i.e., intra-arterially, intravenously, intraperitoneally, subcutaneously, or intramuscularly. More preferably, the pharmaceutical compositions are administered via aerosol administration or intravenously or intraperitoneally by a bolus injection. Particular formulations which are suitable for this use are found in *Remington's Pharmaceutical Sciences* (17th ed. 1985). Typically, the formulations will comprise a solution of the lipid:nucleic acid complexes suspended in an acceptable carrier, preferably an aqueous carrier.

V. Pharmaceutical compositions

Pharmaceutical compositions comprising the lipid:nucleic acid complexes of the invention are prepared according to standard techniques and further comprise a pharmaceutically acceptable carrier. Generally, normal saline will be employed as the pharmaceutically acceptable carrier. Other suitable carriers include, e.g., water, buffered water, isotonic solution (e.g., dextrose), 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipid:nucleic acid complex suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of lipid:nucleic acid complexes in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, immuno-lipid:nucleic acid complexes composed of irritating lipids may be diluted to low concentrations to lessen inflammation at the site of administration. The amount of lipid:nucleic acid complex administered will depend upon the particular Fab' used, the disease state being treated, and the judgement of the clinician. Generally the amount of lipid:nucleic acid complexes administered will be sufficient to deliver a therapeutically effective dose of the nucleic acid. The quantity of lipid:nucleic acid complex necessary to deliver a therapeutically effective dose can be determined by one skilled in the art. Typical lipid:nucleic acid complex dosages will generally be between about 0.01 and about 50 mg nucleic acid per kilogram of body weight, preferably between about 0.1 and about 10 mg nucleic acid/kg body weight, and most preferably between about 2.0 and about 5.0 mg nucleic acid/kg of body weight. For administration to mice, the dose is typically 50–100 µg per 20 g mouse.

VI. Assaying blood half-life

One aid for lipid:nucleic acid complex localization in a target tissue is an extended lipid:nucleic acid complex lifetime in the bloodstream following administration. One measure of lipid:nucleic acid complex lifetime in the bloodstream is the blood/RES ratio determined at a selected time after complex administration. Typically lipid:nucleic acid complexes containing a label (e.g., fluorescent marker, electron dense reagent, or radioactive marker), either internal in the complex or bound to a lipid comprising the complex are injected into the test organism. A fixed period of time later, the organism is sacrificed and the amount of label detected in the blood (e.g., by measuring luminescence, or scintillation counting) is compared to that localized in particular tissues (e.g., liver or spleen).

The time course of retention of lipid:nucleic acid complexes in the blood may also simply be determined by sampling blood at fixed intervals after administration of label-containing lipid:nucleic acid complexes and determining the amount of label remaining in the circulation. The result may be expressed as the fraction of the original dose.

VII. Assaying tissue transfection by the lipid:nucleic acid complexes

Transfection of target cells by the lipid:nucleic acid complexes of this invention may similarly be determined by administering lipid:nucleic acid complexes containing a nucleic acid that is itself detectable or that encodes a detectable product. Biological samples (e.g., tissue biopsies or fluid samples) are then collected and assayed for transfection by detecting the presence of the transfected nucleic acid itself or by detecting the presence of the expressed product of the nucleic acid.

The nucleic acid itself can be selected to have a sequence that is readily detectable, e.g., by nucleic acid amplification. In this instance, the nucleic acid would be selected that has primer sites selected so as to permit unique amplification of the subject nucleic acid and no other in the sample of the biological tissue that is to be assayed for transfection.

Means for detecting specific DNA sequences are well known to those of skill in the art. For instance, oligonucleotide probes chosen to be complementary to a select subsequence with the region can be used. Alternatively, sequences or subsequences may be amplified by a variety of DNA amplification techniques including, but not limited to polymerase chain reaction (PCR) (Innis et al., *PCR Protocols: A guide to Methods and Application* (1990)), ligase chain reaction (LCR) (see Wu & Wallace, *Genomics* 4: 560 (1989); Landegren et al., *Science* 241: 1077 (1988); Barringer et al., *Gene* 89: 117 (1990), transcription amplification (Kwoh et al., *Proc. Natl. Acad. Sci. USA* 86: 1173 (1989)), and self-sustained sequence replication (Guatelli et al., *Proc. Nat. Acad. Sci. USA* 87: 1874 (1990)).

In a particularly preferred embodiment, transfection is evaluated by detecting the presence or absence or quantifying a gene product in one or more tissues. Any gene that expresses an easily assayable product will provide a suitable indicator for the present assay. Suitable reporter genes are well known to those of skill in the art. They include, but are not limited to, bacterial chloramphenicol acetyl transferase (CAT), beta-galactosidase, or luciferase (see, e.g., Alam et al., *Analytical Biochemistry* 188: 245–254 (1990)). One particularly preferred reporter gene is the Fflux gene as illustrated in the Examples.

VIII. Assaying shelf life

As indicated above, the term "shelf life" is used herein to refer to the period of time the lipid:nucleic acid complex can be stored (under defined conditions e.g., in a buffer at 4° C.) before losing its biological activity. The biological activity assayed for determination of shelf life in the present invention is the ability of the lipid:nucleic acid complex to transfect mammalian cells in vivo after intravenous administration.

In a preferred embodiment the shelf life is determined by storing the lipid:nucleic acid complexes for varying periods of time, injecting one or more test animals with the complex and assaying selected tissues in the animal for transfection (e.g., expression of a reporter gene) as described above and as illustrated in the examples.

It will be appreciated that shelf life can be expressed in absolute terms, i.e., the length of time the composition can be stored before losing activity. Alternatively, shelf life can be expressed in relative terms by reference to a different composition. Thus, for example, when the subject complex shows transfection activity after a fixed period of storage and this activity is greater than the activity of a different complex similarly stored for the same amount of time, the subject complex is said to have an increased shelf life as compared to the different complex.

IX. Targeting lipid:nucleic acid complexes to specific tissues

Specific targeting moieties can be used with the lipid:nucleic acid complexes of the invention to target specific cells or tissues. In one embodiment, the targeting moiety, such as an antibody or antibody fragment, is attached to a hydrophilic polymer and is combined with the lipid:nucleic acid complex after complex formation. Thus, the use of a targeting moiety in combination with a generic effector lipid:nucleic acid complex provides the ability to conveniently customize the complex for delivery to specific cells and tissues.

Examples of effectors in lipid:nucleic acid complexes include nucleic acids encoding cytotoxins (e.g., diphtheria toxin (DT), Pseudomonas exotoxin A (PE), pertussis toxin (PT), and the pertussis adenylate cyclase (CYA)), antisense nucleic acid, ribozymes, labeled nucleic acids, and nucleic acids encoding tumor suppressor genes such as p53, p110Rb, and p72. These effectors can be specifically targeted to cells such as cancer cells, immune cells (e.g., B and T cells), and other desired cellular targets with a targeting moiety. For example, as described above, many cancers are characterized by overexpression of cell surface markers such as HER2, which is expressed in breast cancer cells, or IL17R, which is expressed in gliomas. Targeting moieties such as anti-HER2 and anti-IL17R antibodies or antibody fragments are used to deliver the lipid:nucleic acid complex to the cell of choice. The effector molecule is thus delivered to the specific cell type, providing a useful and specific therapeutic treatment.

X. Lipid:nucleic acid complex kits

The present invention also provides for kits for preparing the above-described lipid:nucleic acid complexes. Such kits can be prepared from readily available materials and reagents, as described above. For example, such kits can comprise any one or more of the following materials: liposomes, nucleic acid (condensed or uncondensed), hydrophilic polymers, hydrophilic polymers derivatized with targeting moieties such as Fab' fragments, and instructions. A wide variety of kits and components can be prepared according to the present invention, depending upon the intended user of the kit and the particular needs of the user. For example, the kit may contain any one of a number of targeting moieties for targeting the complex to a specific cell type, as described above.

The kit may optionally include instructional materials containing directions (i.e., protocols) providing for the use of the cationic lipid:nucleic acid complex for transfecting cells in vivo, ex vivo, or in vitro. Typically, the instruction materials describe the procedure for preparing the lipid-:nucleic acid complex from liposomes and nucleic acid, as described above. The instruction materials also describe how to mix the hydrophilic polymer with the lipid:nucleic acid complex. Additionally, the instruction materials can describe procedures for transfecting cells with the lipid-:nucleic acid complex.

While the instructional materials typically comprise written or printed materials, they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

XI. Preparation of lipidic microparticles with surface attached proteins

A. General

The present invention also provides for the preparation of lipidic microparticles with surface-attached proteins. As noted in the Background section, above, the art teaches that soluble proteins such as antibodies are so large that their tendency to solubilize overwhelms the tendency of a hydrophobic domain of a linker molecule attached to the protein to become stably associated with a lipidic microparticle. The teaching has therefore been that, while small peptides conjugated to a linker molecule of approximately the same size or larger might permit the hydrophobic domain of a linker molecule to become stably associated with a lipidic microparticle, proteins conjugated to a linker molecule, which is much smaller than the protein, would not be able to do so.

We have now found that, contrary to the teachings of the art, proteins many times larger than a linker molecule can be conjugated to a linker molecule and still be successfully and stably attached to a lipidic microparticle. The Examples, below, demonstrate that proteins many times larger than the linker molecules to which they are conjugated can be successfully attached to lipidic microparticles. This discovery expands the types of agents with which such microparticles can be loaded. Further, it expands the range of methods by which such microparticles can be made and still attached to proteins, since the attachment can now take place under conditions where the stability of the microparticle, such as a liposome, will not be jeopardized.

Preferably, the proteins used in this method have a molecular weight between about 6,000 and about 1,000,000 Daltons. More preferably, the proteins have a molecular weight between about 10,000 and about 600,000 Daltons. Even more preferably, the proteins have a molecular weight between about 15,000 and about 250,000 Daltons. Most preferably, the proteins have a molecular weight between about 20,000 and about 75,000 Daltons B. Attachment of proteins by incubating lipidic microparticles with proteins conjugated to linker molecules For use in this invention, a protein can first be conjugated to a linker molecule comprising (a) a hydrophobic domain, (b) a hydrophilic polymer chain terminally attached to the hydrophobic domain, and (c) a chemical group reactive to one or more functional groups on a protein molecule and attached to the hydrophilic polymer chain at, or near to, the terminus contralateral to the hydrophobic domain. Such linker molecules are known in the art (Allen & Martin, U.S. Pat. No. 5,527,528; Shahinian & Sylvius, *Biochim. Biophys. Acta,* 1239:157–167 (1995); Zalipsky et al., *J. Controlled Release* 39:153–161, 1996; Kirpotin et al., *Biochemistry,* 36:66–75 (1997)).

The hydrophobic domain of the linker molecule may be, for example, a diacylglycerol, a phospholipid, a sterol, such as cholesterol, or a diacylamide derivative, such as N,N-distearoyl-glycineamide. The hydrophilic polymer chain may be, for example, poly(ethylene glycol), polyglycidol, poly(vinyl alcohol), poly(vinyl pyrrolidone), polyoxazolidinone, polysaccharide, or a copolymer which includes the blocks of the above polymers. The chemical reactive group may be, for example, an amino group, carboxy group, thiol group, malemido group, iodoacetamido group, vinylsulfone group, aldehyde group, hydrazine group, ketone group, cyanure chloride group, or any other functional group known in the art to form linkages with proteins. A protein may be an antibody, an enzyme, a growth factor, a hormone, a nucleic acid-binding protein, or any other protein of utility for a particular intended application.

In a preferred embodiment of the invention, the protein is an Fab" fragment of an antibody, or a single chain antibody. In a further preferred embodiment, the single chain antibody is a Fv antibody produced through selection from a phage display library. Maleimido groups, which react with cysteine residues in the protein, are preferred as the reactive group for use with an Fab' antibody fragment or single chain antibody.

The conjugation of the protein to the linker can be effected by any of a number of methods known in the art for protein conjugation. In a preferred method, the linker can be simply dissolved in aqueous buffer (which is possible due to the presence of the hydrophilic polymer domain) and incubated with the protein of choice to afford formation of a stable bond between the chemical reactive group of the linker and the appropriate functional group of the protein. The conjugate can be further purified from the excessive linker and any unconjugated protein by salting-out, dialysis, chromatography and other methods known in the art of protein purification. Alternatively, the conjugate can be used without further purification.

Conjugated protein is then incubated with the lipidic microparticles in an aqueous medium for a time sufficient for the hydrophobic domain of the conjugate to merge into the surface lipid layer of the particle. The time required will depend on the lipid composition of the microparticle, the nature of the hydrophobic domain, and the temperature of incubation. Typically, the time of incubation will lie in the range from about 1 minute to about 50 hours. The time necessary for incubation will decrease as the temperature at which the incubation is conducted is increased. Thus, at 37° C., the incubation will generally take overnight, while at 55–60° C., the incubation will generally take 5–60 minutes, with 15–30 minutes being preferred. Incubation times appropriate for any particular combination of microparticle, hydrophobic domain, and temperature, can be determined using the assays taught in the Examples, below.

C. Preparation of proteins containing hydrophobic domains which will self-insert into a lipidic microparticle In an alternative embodiment, a hydrophobic anchor and a hydrophilic polymer chain are introduced into a protein molecule by recombinant DNA and protein engineering methods. In this case, a hydrophilic polymeric domain, as described above, is introduced into the protein of interest by a terminally appended polyaminoacid sequence containing primarily amino acids with hydrophilic side chains. A hydrophobic anchor is introduced into the construct during its biosynthesis via a lipid modification site positioned at the distal end of the terminally appended polyaminoacid sequence.

EXAMPLES

The invention is illustrated by the following examples. These examples are offered to illustrate, but not to limit the present invention.

Example 1
Preparation of stable lipid:plasmid DNA complexes for in vivo gene delivery A. Materials and methods 1. Lipids & other reagents DOPE was purchased from Avanti (Alabaster, Ala.). Highly purified Cholesterol was obtained from Calbiochem (San Diego, Calif.). DDAB and dextran (M.W. 40,000) were purchased from Sigma (St. Louis, Mo.). DDAB was recrystalized once from acetone-methanol solution. D-luciferin was obtained from Boehringer Mannheim. PEG-PE was a gift from Sequus Pharmaceuticals (Menlo Park, Calif.). DC-Chol, MMCE and DOGS were obtained from UCSF Gene Transfer Vehicle Core of Gene Therapy Center. ESPM, DOTAP, POEPC, DOEPC, DMEPC and DODAP were gifts from Avanti (Alabaster, Ala.). Chloroform solution of each lipid was stored under argon in sealed ampules at −40° C. Other reagents of possible highest grade were purchased and used without further purification.

2. Preparation of liposomes

Small cationic liposomes were prepared in 5% (w/v) dextrose solution in the following fashion. DDAB or other cationic lipids in chloroform was mixed with DOPE or/and cholesterol in a desired molar ratio, and the solvent was removed slowly under reduced pressure at 50° C. on a rotary evaporator. The dry lipid film was hydrated with 5% dextrose solution prewarmed to 50° C. and the container was sealed under argon. The hydrated lipid suspension was sonicated in a bath sonicator (Lab Supplies, Hicksville, N.Y.) for 5–10 min at 50° C. The final concentration of liposomes was 5 mM cationic lipid and the size of liposomes was measured by dynamic light scattering to be 195±65 nm. Sonicated liposomes were stored under argon at 4° C. until use.

3. Luciferase reporter system

Plasmid, pCMV/IVS-luc$^+$, was constructed as follows. A fragment containing the CMV promoter and synthetic IgE intron was excised from pBGt2.CAT using Spe I and Hind III and cloned into pBSIIKS$^+$. The cDNA encoding the modified firefly luciferase (luc+) including SV40 late poly (A) signal was cut from the pGL3-Basic Vector (Promega) with Hind III and Sal I and was put into the pBS-CMV-IVS clone downstream of the splice. Plasmids were purified using alkaline lysis procedures adopted and devised by Qiagen Corp. (Chatsworth, Calif.). Plasmid purity was measured by the ratio of absorbance at 260 nm vs 280 nm, and stored in buffer containing 10 mM Tris-Cl and lmM EDTA at pH 8.0 at concentrations of 1–2 mg/ml.

4. Preparation of transfection complexes

Prior to the transfection experiments, the optimal DNA/liposome ratio for forming complexes which were not large aggregates was determined by mixing fixed amount plasmid to various amount of liposomes. In general, the transfection complexes were formed by pipetting plasmid into liposome suspension of equal volume and mixing rapidly. Routinely, liposomes containing 8–12 nmole of DDAB could complex with 1 $\mu$g plasmid without forming visible large aggregates. Such complexes have excess positive charge, but still tend to aggregate with time during storage at 4° C. and lose transfection activity in 4 days. For in vitro experiments, which called for much dilute complexes, cationic lipid:plasmid DNA complexes ("CLDC") at 5 nmole DDAB per $\mu$g DNA were used. To keep the lipid:plasmid DNA complexes from forming large aggregates and losing transfecting activity with time, two approaches were taken: (1) incorporating a small amount of PEG-PE (approx. 1% mole ratio) into lipid:plasmid DNA complexes within a few minutes after their preparation; and/or (2) condensing plasmid with polyamines (e.g., 0.05 to 5.0 nmole of spermidine per $\mu$g DNA) prior to mixing with liposomes. The optimal amount of the polyamines was determined by titrating polyamines to DNA before forming large aggregates. The size of these complexes was estimated by dynamic light scattering to be in the range of 410±150 nm.

5. Assay of reporter gene expression

Purified luciferase was purchased from Boehringer Mannheim as a standard for calibrating the luminometer and constructing a control standard for the relative specific activity of luciferase. Reporter gene expression in a tissue extract was presented in nanogram quantities by converting relative light unit measured from a luminometer into weight unit according to a standard curve. Luciferase expressed in cells or tissues was extracted with chemical cell lysis. Effective lysis buffer consisted of 0.1 M potassium phosphate buffer at pH 7.8, 1% Triton X-100, 1 mM DTT and 2 mM EDTA.

Female CD1 mice (4–6 weeks old, weighing approx. 25 g) were obtained from Charles River Laboratory. Mice received lipid:plasmid DNA complexes by tail vein injection and were sacrificed 24 h later. The anesthetized animals were perfused with cold phosphate-buffered saline (PBS) via heart puncture. Each tissue was dissected and washed in PBS, and then homogenized in 6 ml round-bottomed culture tube containing 500 $\mu$l of lysis buffer. The samples were kept at room temperature for 20 min with occasional mixing. The homogenized samples were centrifuged for 10 min at 3000 rpm in an Eppendorf centrifuge. Luciferase activity of each tissue was measured by mixing 100 Al of the reconstituted luciferase substrate (Promega, Madison, Wis.) with 20 $\mu$l of the supernatant of tissue homogenate in the injection system of a luminometer. Peak light emission was measured for 10 sec. at 20° C. Relative light units of each sample were converted to the amount of luciferase in the tissue extract by comparing with a standard curve which was established for each set of experiments. The protein content of the extract was determined using protein assay kits (BioRad, Richmond, Calif.). Background was the count of lysis buffer only.

SK-BR-3 cells (Park et al., *Proc. Natl. Acad. Sci. USA* 92: 1327–1331 (1995)) were cultured in McCoy's 5 A medium supplemented with 10% heat-inactivated bovine calf serum and in 5% $CO_2$. SK-BR-3 cells in monolayer culture were plated at 50,000 cells per well in 12-well plates and incubated overnight. Each well received 0.5~1 $\mu$g of pCMV/IVS-luc$^+$ within 20 min of complex formation. Cells were harvested after 24 hr of incubation with complexes at 37° C. Luciferase activity in cells was determined as described above.

B. Results

1. Optimizing the "helper" lipid

The use of cationic liposomes for in vitro gene transfer has become widespread since Felgner et al. published their study (Felgner et al., *Proc. Natl. Acad. Sci. USA* 84: 7413–17 (1987)). It was established later (Felgner et al., *J. Biol. Chem.* 269: 2550–2561 (1994)) that DOPE is by far the most efficient "helper" lipid for in vitro gene transfection and this result has confirmed by several laboratories (Farhood et al., in *Gene Therapy for Neoplastic Diseases,* pp 23–55 (Huber & Lazo eds., 1994); Zhou et al., *Biochim. Biophys. Acta* 1189: 195–203 (1994)). It has been suggested, on the basis of in vitro studies, that DOPE may facilitate the cytoplasmic delivery via membrane fusion once positively charged lipid:plasmid DNA complexes are bound to the cell membrane (Zhou et al., *Biochim. Biophys. Acta* 1189: 195–203 (1994)). Even though Friend et al. did not obtain any morphological evidence that the DOTMA/DOPE lipid:plasmid DNA complexes fuse directly with the plasma membrane, they do not exclude the possibility of fusion events (Friend et al., *Biochim. Biophys. Acta* 1278: 41–50 (1996)). They suggested that the complexes are endocytosed and the cationic lipids disrupt the endosomal/lysosomal membranes and then facilitate an escape of the DNA complexes into the cytoplasm and eventually into the nucleus.

Figure 1B:
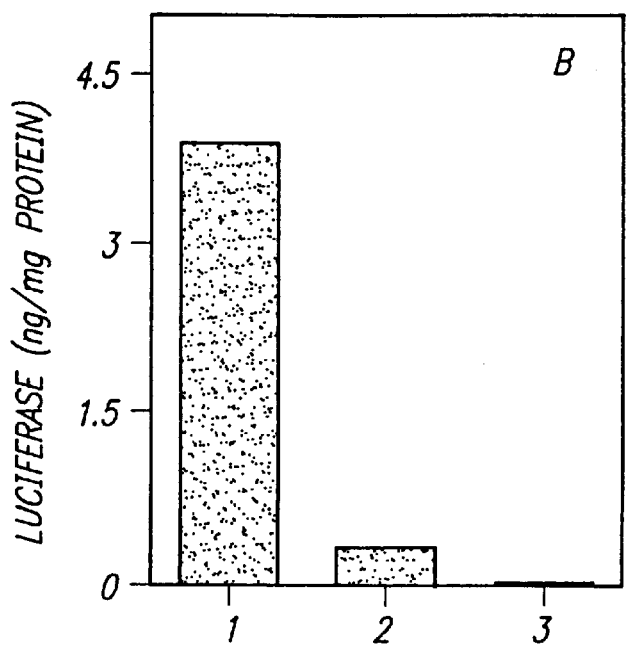

Contrary to most expectations, the "helper" role of DOPE established from in vitro studies is not evident for in vivo gene delivery following i.v. injection of the complexes. When DOPE was included in DDAB cationic liposomes, the in vivo gene transfection was inhibited. This DOPE-dependent inhibition is shown in FIG. 1. Cholesterol, not DOPE, was found to be effective as "helper" lipid for in vivo gene delivery. There was a ten-fold reduction in luciferase expression in mouse lungs when half of the cholesterol was replaced with DOPE. The in vivo results of DDAB and other cationic liposomes are not consistent with the general assumption that DOPE is a suitable "helper" lipid. On the contrary, DOPE in cationic lipid:plasmid DNA complexes attenuates the in vivo transfection to such a great degree that DOPE is considered as an inhibitory agent in formulations for in vivo gene delivery. Cholesterol has been chosen for in vivo studies in recent published reports (Liu et al., *J. Biol. Chem.* 270: 24864–70 (1995); Solodin et al., *Biochemistry* 34: 13537–44 (1995)) in which the authors do not elaborate on how and why they selected different "helper" lipids for their experimental designs, i.e. DOPE for in vitro and cholesterol for in vivo studies. Stabilization of anionic and neutral liposomes in blood by cholesterol has been known for a long time (Mayhew et al., *Cancer Treat. Rep.* 63: 1923–1928 )1979)). It is therefore obvious that for systemic gene delivery, one has to consider the stability of lipid:plasmid DNA complexes in blood, various components of which are known to react with macromolecular complexes. In fact, the preliminary study of various formulations of lipid:plasmid DNA complexes using freeze-fracture electron microscopy has shown that the cholesterol-containing complexes were structurally more stable than the DOPE-containing complexes in the presence of serum.

Figure 2:
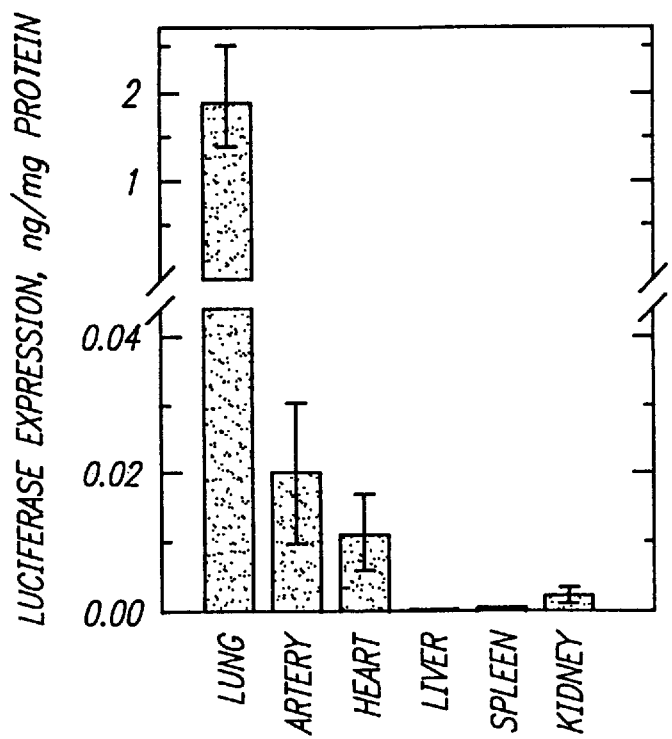
FIG. 2 illustrates reporter gene expression in mouse tissue extracts. Mice received (via tail vein injection) 60 μg of P-CMVIVS-Luc+plasmid, which was complexed with DDAB/Chol (1:1) liposomes at 8-nmole DDAB per μg DNA ratio (without spermidine). Values presented are mean from 3 mice.
Figure 3:
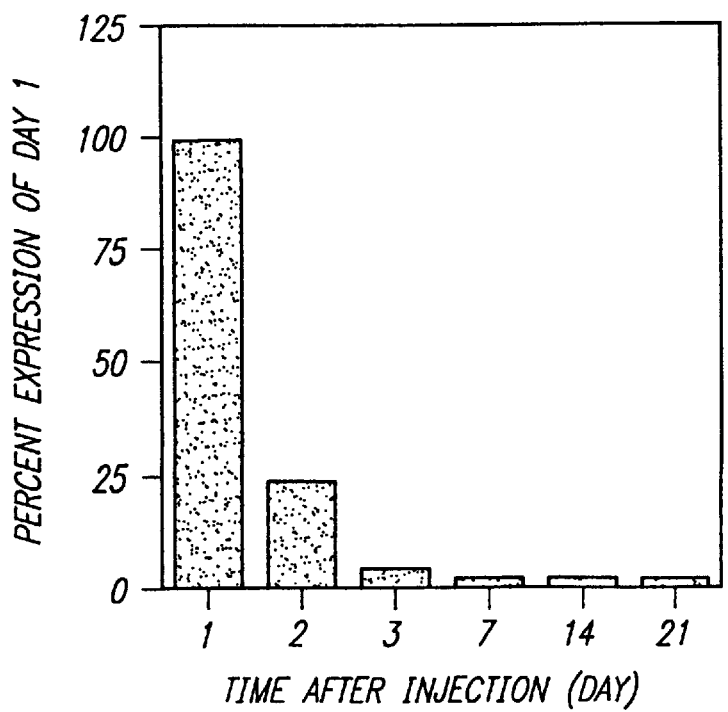
FIG. 3 illustrates the duration of reporter gene expression in mouse luna. Each animal received 40 μg of P-CMVIVS-Luc+plasmid, which was complexed with DDAB/Chol (1:1) liposomes at 8 nmole DDAB per μg DNA ratio.

Using DDAB/Chol lipid:plasmid DNA complexes (8 nmole DDAB/µg DNA) for in vivo transfection experiments, detectable luciferase expression in the lung of 25 g mouse required a DNA dose ranging from 30 µg to 60 µg. Routinely 40–60 µg plasmid DNA per mouse gave consistent gene expression. The amount of DDAB usually associated with 80 µg DNA (or more) per mouse was found to be too toxic to the animal. The expression of luciferase in various tissues is shown in FIG. 2. As observed before (Zhu et al., *Science* 261: 209–211 (1993); Liu et al., *J. Biol, Chem.* 270: 24864–70 (1995); Solodin et al., *Biochemistry* 34: 13537–44 (1995)), maximal expression was found in lung tissue. For 60 µg plasmid injected, 1–2 µg luciferase per mg tissue protein was routinely obtained. FIG. 3 shows the duration of reporter gene expression in lung tissue. Expression of luciferase decreased rapidly and reached undetectable levels in 2 weeks. Zhu et al. reported that following i.v. injection of DOTMA/DOPE (1:1)—plasmid complexes into adult mice, the expression of the reporter gene (CAT) is widespread among various tissues and the maximum expression is from complexes with a ratio of 1 I µg plasmid to 8 nmole total lipids (Zhu et al., *Science* 261: 209–211 (1993)). However, at this ratio (corresponding to 1 µg plasmid to 4 nmole cationic lipid), DDAB/Chol lipid:plasmid DNA complexes tended to aggregate and did not produce measurable gene expression in this investigation.

Since different reporter genes have been used among different laboratories, it has been difficult to attribute the variations in the efficiency of in vivo gene delivery to changes in the formulation of liposomes. For a direct comparison of the results in the literature, the relative light units of luciferase activity measured from a luminometer was converted to a standard of purified luciferase. By doing so, the peak transfection activity of DDAB/Chol formulations was 3 orders of magnitude higher than values reported recently in comparable experiments (Thierry et al., *Proc. Natl. Acad. Sci. USA* 92: 9742–9746 (1995)). Given that same reporter gene along with same promoter in the experimental design, the difference in expression may reflect the selection of liposome formulation. In fact, DDAB/Chol was one of the most efficient gene delivery vehicle among many formulations from 18 different cationic lipids which was screened recently. Preliminary results of expression in mouse lung following i.v. injection indicated that DOTMA/Chol, DOTAP/Chol, MMCE/Chol and ESPM/Chol gave 10–100% transfection activity of DDAB/Chol, DOGS/Chol, POEPC/Chol, LYSPE/DOPE and DC-Chol/DOPE gave 1–10% of DDAB/Chol. DOEPC/Chol, DMEPC/Chol, DODAP/Chol and DDAB/DOPE did not give any measurable activity.

In parallel with the transfection studies, the morphology of these complexes in serum and in cell medium was examined by freeze-fracture electron microscopy. When examined in 50% mouse serum (10 minute incubation time), non-stabilized, one day old CLDC are as small as they are in buffer at low ionic strength (100–250 nm) but show very few protrusions. Six day old, non stabilized CLDC incubated in 50% mouse serum appeared as densely packed aggregates of spherical particles, with a high number of attached particles. Such formulations have lost all of their in vivo transfection activity within 4 days. Residual fibrillar protrusions are not observed.

PEG-PE stabilized CLDC incubated in 50% mouse serum were small (100–200 nm) even at six days. Similarly, CLDC prepared with condensed DNA were also quite small even after six days of storage. Specifically, the CLDC were shaped like "map pins" that were structurally stable in the presence of serum.

After incubation in cell medium (RPMI-1640 with 10% FCS), non-stabilized six day old CLDC were morphologically similar to those incubated in mouse serum, as described above. These complexes, however, were more loosely packed and showed no fibrillar protrusions. Similar morphology was observed with PEG-PE stabilized CLDC and condensed DNA CLDC incubated in cell medium.

2. Increasing shelf life for transfection activity

Figure 4:
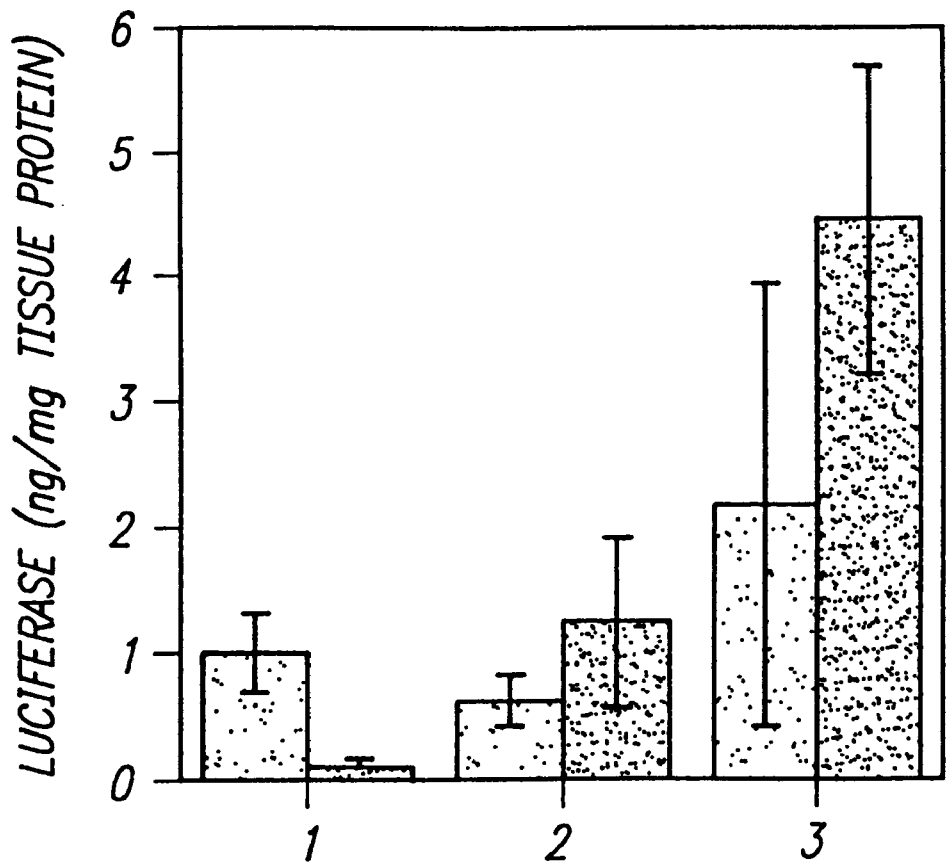
FIG. 4 illustrates gene delivery in mouse lung by various stabilized complexes. Each mouse received 60 μg of P-CMVIVS-Luc+, which was complexed with DDAB/Chol (1:1) liposomes at 8 nmole DDAB/μg DNA ratio. Values presented are mean from 3 mice. Stippled bars: freshly made complexes; filled bars; one month-old samples. Samples are as follows: (1) No stabilizing agent was added; (2) PEG-PE was added at 1% of total lipid to the formed complexes; and (3) Spermidine (0.5 nmole per μg DNA) was added to the plasmid prior to the complex formation.

The relationship between structural stability and transfection activity of lipid:plasmid DNA complexes has not been detailed in the published reports so far. Screening procedures have been established to avoid large aggregates of lipid:plasmid DNA complexes by changing the ratio of DNA to lipid from net negatively charged to positively charged. Lipid:plasmid DNA complexes of each particular cationic lipid at various ratios of DNA/lipid were prepared and the resulting stable and metastable formulations were used for in vivo transfection. Complexes which contained 8 to 12 nmole of cationic lipid per Ag DNA were found to have the highest in vivo transfection activity. However, the transfection activity of these complexes decreased with time. Without modifying the procedures of forming the lipid:plasmid DNA complexes, there was a visible aggregation within a few days, and the transfection activity decreased by more than a thousand fold to almost background levels after one month's storage at 4° C. (FIG. 4). Therefore, formulation of stabilized lipid:plasmid DNA complexes was undertaken, which could maintain high in vivo transfection activity during storage.

i. Increasing transfection stability: PEG-PE

Inserting PEG-PE (1% of total lipid) into the freshly formed lipid:plasmid DNA complexes not only could prevent the complexes from aggregating during storage, but the PEG-PE containing complexes also exhibited reasonably high transfection activity in vivo, only slightly lower activity as compared to the complexes without PEG-PE (FIG. 4). Incorporation of PEG-PE into the complexes is evident in view of the dose-related inhibition of the transfection activity with increasing percentage of PEG-PE (results not shown). Unexpectedly, storage of the complexes containing PEG-PE at 4° C. slyly restored the original activity, as shown in FIG. 4. The mechanistic aspects of the inhibition effect on transfection by PEG-PE, as well as the recovery of the activity following storage at low temperature, are not known at present time.

ii. Increasing transfection stability: polyamines

In addition to the role of PEG-PE in increasing the shelf life of lipid:nucleic acid complexes, condensing nucleic acid with polyamines also gave a similar unexpected increase in shelf life of the complexes. The lipid:plasmid DNA complexes formed with condensed DNA were stable at a lower ratio of lipid to DNA without aggregation. FIG. 4 shows the level of in vivo transfection activity of such preparation, and its fate during storage. Again, an unexpected increase of the transfection activity was found in aged polyamine-treated lipid:plasmid DNA complexes, when compared to that of the samples which were not pretreated with polyamines and used immediately after complexes were formed. A different approach to obtain stable cationic lipid/DNA complexes by complexing plasmid with lipid in lipid-detergent micelles was published recently (Hofland et al., *Proc. Natl. Acad. Sci. USA* 93: 7305–7309 (1996)). However, only 30% of the transfection efficiency was maintained by such complexes in 15% serum for in vitro, and no in vivo results were reported.

iii. Increasing transfection stability: lyophilization

Finally, conditions have been established for the stabilization of lipid:plasmid DNA complexes by lyophilization. Liposomes composed of DDAB/Chol suspended by sonication in 5% (w/v) of dextran in water, when mixed with DNA in 1:10 ratio ($\mu$g DNA per nmole DDAB) as described in methods, could be lyophilized without loss of activity. The final concentration of dextran in which lipid:plasmid DNA complexes were formed was 8% (w/v). The lyophilized preparations were reconstituted by adding distilled water and their transfection activity in the lungs of mice after i.v. injection was measured by luciferase reporter gene expression. Freezing and thawing the reconstituted preparation did not affect the activity (usually 1–2 ng luciferase protein per mg tissue protein).

Several of the cationic lipid:plasmid DNA complexes described herein are stable and can give consistent in vivo transfection activity (ranging from 0.5 to 2 ng luciferase per mg tissue protein) even after long storage at 4° C. or lyophilization. Formulations containing cholesterol as the "helper" lipid generate much higher in vivo transfection efficiency. Stabilizing the complex structure by PEG-PE maintains the complex activity in storage and may prolong the circulation time in blood for targeting to specific tissues. Condensing the DNA with polyamines before lipid complexation enhances in vitro storage and levels of activity in vivo. The methodical approach for producing stable formulations of lipid:plasmid DNA complexes exhibiting high transfection activity in vivo confers advantages for establishing pharmaceutically acceptable preparations, and therefore facilitates liposome based gene therapy.

Example 2

In vitro transfection of lipid:plasmid DNA complexes with targeting ligands

A. Preparation of Fab' fragments

Cloned rhuMAbHER2 sequences for heavy and light chain were co-expressed in *E. coli* as previously described (Carter et al., *Biotechnology* 10: 163–167 (1992)). The antibody fragment, rhuMAbHER2-Fab', was recovered from *E. coli* fermentation pastes by affinity chromatography with Streptococcal protein G (Carter et al., *Biotechnology* 10:163–167 (1992)), typically yielding Fab' with 60–90% containing reduced free thiol (Fab'-SH).

B. Preparation of liposomes

Condensed DNA was complexed with three different lipid compositions, using the methods described above in Example 1, with the following modifications. The first complex was made with DDAB/DOPE (1/1), which produced cationic liposomes complexed with DNA only, as described above. The second complex was made with DDAB/DOPE (1/1) with 1% PEG-PE derivatized with maleimide at the ultimate position of PEG, producing CLDC with the steric stabilization component added after complexation with the DNA. The third complex was made with DDAB/DOPE (1/1) with 1% PEG-PE derivatized with the Fab' fragment of a humanized anti-Her-2 antibody attached to the ultimate position of PEG via the free thiol group to the maleimide residue. This produced CLDC with the targeting ligand attached to the steric stabilization component added after the complexation with the DNA.

C. Transfection and results

Cells were transfected as described above in Example 1, but without storage of the lipid:plasmid DNA complex. Two cell lines were used in this Example. The first cell line was MCF-7; cells of this cell line do not overexpress the HER-2 receptor. These cells were cultured in DME H-21 with 10% bovine calf serum and in 5% $CO_2$. The second cell line was SK-BR3 cells, cells of which overexpress the HER-2 receptor, cultured in McCoy's 5A medium with bovine calf serum in 5% $CO_2$. In both cases, the cells (~5×10$^4$ cells per well) were transfected and incubated with 12 $\mu$g plasmid DNA complexed with lipid as described above (PCMV/IVS-luc+, luciferase reporter gene described above) for 4 hours at 37° C. The supernatant was then aspirated, fresh medium was added and the cells were incubated for 24 hours at 37°

C. Cells were then harvested by washing with PBS (Ca/Mg free) and then suspended in lysis buffer for the luciferase assay, as described above.

Figure 5A:
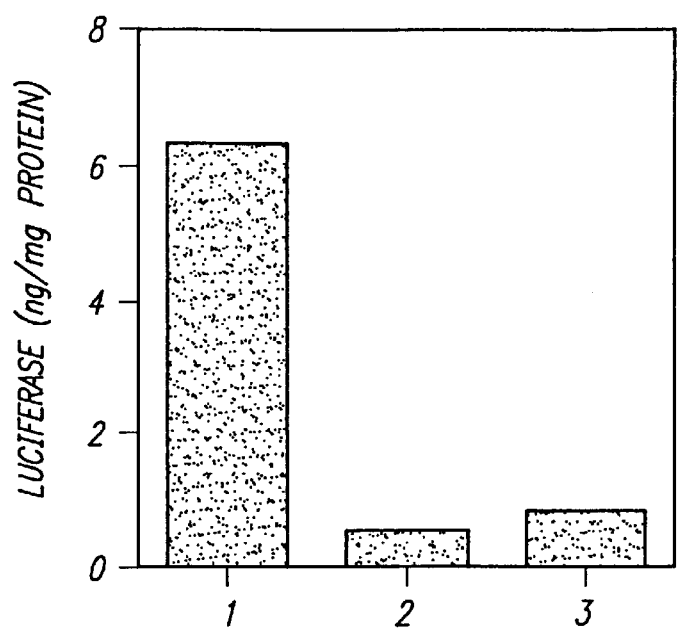
FIGS. 5A and 5B illustrate in vitro transfection of cell lines with immunolipid:DNA complexes. The samples are as follows: (1) DDAB/DOPE (1:1), producing cationic liposomes complexed with DNA only; (2) DDAB/DOPE (1:1) with 1% PEG-PE derivatized with maleimide at the ultimate position of PEG, producing liposomes with the steric stabilization component added after complexation with the DNA; and (3) DDAB/DOPE (1:1) with 1% PEG-PE derivatized with the Fab' fragment of a humanized anti-Her-2 antibody attached to the ultimate position of PEG via the free thiol group to the maleimide residue.
Figure 5B:
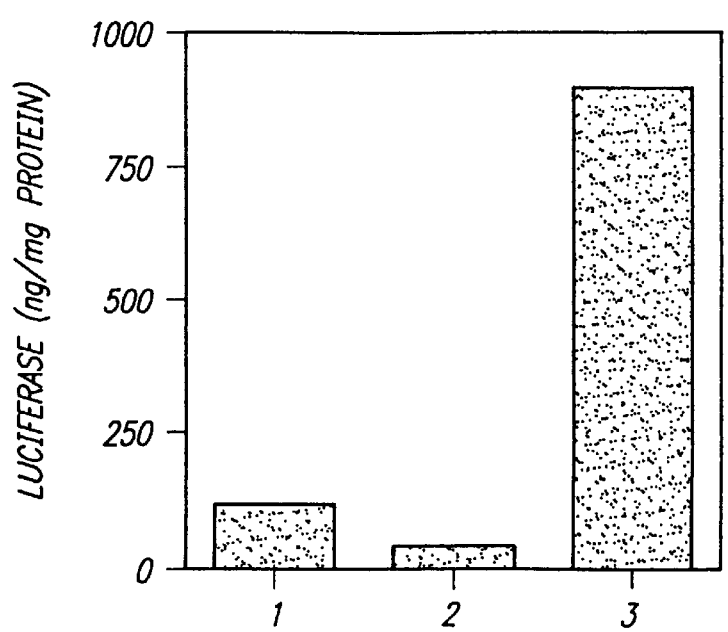

FIG. 5A shows that transfection of non-target cells, not over-expressing the HER-2 receptor, was inhibited by the addition of PEG-PE, even in the presence of the targeting ligand conjugated at the tip of PEG via the terminal maleimide residue. FIG. 5B shows that transfection of target cells overexpressing the HER-2 receptor was also inhibited by the addition of PEG-PE, but the transfection activity was restored and augmented when the PEG-PE was conjugated to a targeting ligand, which recognizes the HER-2 receptor.

Comparison of FIGS. 5A and 5B indicates that the targeted immuno-CLDC were active in transfecting target cells much more efficiently than non-target cells. This result occurs because the addition of the ligand-carrying stabilizing agent (PEG-PE) conjugated to anti-HER-2-Fab'), which inhibits the transfection of non-target cells (FIG. 5A) but augments transfection of the target cells (FIG. 5B).

Example 3
Preparation of the linker maleimido-propionylantido-PEG2000-distearoylphosphatidylethanolamine (Mal-PEG-DSPE).

100 mg (44 mol) of ω-maleimidopropionylamido-poly (ethylene glycol)-α-succinimidylcarbonate (Mal-PEG-NHS; Shearwater Polymers, Inc.) prepared from poly (ethylene glycol) (molecular weight 2,000), 33 mg (44 $\mu$mol) of distearoyl-phophatidylethanolamine (DSPE; Avanti Polar Lipids), and 12 ml (86 $\mu$mol) of triethylamine in 1 ml of chloroform, were incubated for 6 hours at 45° C. At this time, thin layer chromatography on silica (solvent, chloroform/methanol 7:3) indicated complete conversion of DSPE into faster moving, ninhydrin-negative product identified as Mal-PEG-DSPE. This product was purified by column chromatography on silica, using stepwise gradient of methanol in chloroform (5%, 10%, 15% of methanol by volume). Pure Mal-PEG-DSPE was eluted at 15% methanol. Yield, 85 mg (67% of theory). $R_f$ 0.27–0.29 (Silica 60, $CHCl_3$—MeOH—$H_2O$ 65:25:4). Ratio of maleimido groups to phosphate, 0.95–1.02.

Alternatively, this linker may be prepared as described in U.S. Pat. No. 5,527,528 or in Kirpotin et al. (*Biochemistry*, 36:66–75 (1997)).

Example 4
Conjugation of Mal-PEG-DSPE with Fab' fragment of an antibody reactive against HER2 oncoprotein.

300 nmol of Mal-PEG-DSPE in 0.5 ml of chloroform were placed in a glass test-tube and the solvent was removed in vacuum. The dry residue was dissolved in 1 ml of MES-20 buffer (20 mM morpholinoethane sulfonic acid, 144 mM sodium chloride, 2 mM ethylenediamine tetraacetic acid, and NAOH to pH 6.0). 2,5 ml of solution containing 0.57 mg/ml of Fab' fragments of a recombinant humanized monoclonal antibody against extracellular domain of HER2 oncoprotein (rhuMAbHER2, Genentech, Inc.) was added to the Mal-PEG-DSPE solution, and the pH was carefully adjusted to 7.2–7.4 with diluted NaOH. The mixture was incubated under argon at room temperature for 2.5 hours, and the reaction was stopped by addition of 0.2 M cysteine hydrochloride to a final concentration of 5 mM. Fifteen minutes after the addition of cysteine, the reaction mixture was dialyzed against HEPES-buffered saline (20 mM hyrdoxyethylpiperazino ethanesulfonic acid, 144 mM NaCl, NaOH to pH 7.2), concentrated by ultrafiltration through a YM-10 membrane (Amicon) under pressure, and sterilized by filtration through a 0.2 $\mu$m cellulose acetate filter. The reaction products were analyzed by polyacrylamide gel electrophoresis in the presence of sodium dodecyl sulfate (SDS-PAGE), with Coomassie Blue staining. Total protein was determined the dye binding assay (Bio-Rad). The assay revealed 62% conversion of the original protein (M.w. 46,000) into slower-moving product (M.w. 49,000) consistent with the expected conjugate. Total protein recovery in the products was 98%.

Example 5
Conjugation of Mal-PEG-DSPE with a single chain Fv antibody reactive against HER2 oncoprotein.

150 nmol of Mal-PEG-DSPE were dissolved in 0.5 ml of MES-20 and reacted with 0.5 ml of solution containing 0.7 mg/nml of single-chain Fv antibody C6.5Cys reactive against extracellular domain of HER2 oncoprotein. The antibody was prepared as described by Schier et al. (Immunotechnology 1:73–81 (1995)). The reaction and products assay were conducted as described in the Example above. Total protein recovery was 86%. Approximately 52% of the recovered protein (M.w. 27,000) was in the form of a product with higher molecular weight (M.w. 29,000–30,000), consistent with the expected conjugate.

Example 6
Preparation of inimunoliposomes with conjugated anti-HER2 Fab' fragments and loaded with a fluorescent ph-sensitive indicator Small (100 mn) unilamellar liposomes containing entrapped pH-sensitive fluorescent indicator 8-hydroxypyrene trisulfonic acid were prepared from a mixture of 1-palmitoyl-2oleoyl-phosphatidylcholine (Avanti), cholesterol (Calbiochem), and methoxypolyoxyethyleneglycol (M.w. 1,900)-derivatized distearoyl phosphatidylethanolamine (Sygena) in the molar ratio of 30:20:3 as described by Kirpotin et al. (*Biochemistry*, 36:66–75 (1997)), and sterilized by filtration through 0.2 $\mu$m cellulose acetate filter. 0.26 ml of liposome preparation containing 2 $\mu$mol of phospholipids was mixed with 0.106 ml of a solution containing 100 $\mu$g of the anti-HER2 Fab'-PEG-DSPE conjugate prepared according to Example 4, above, and incubated overnight at 37° C. Following incubation, the liposomes were separated from unbound material by gel-filtration on a column with Sepharose 4B (Pharmacia), using HEPES-buffered saline as eluent. The liposomes were eluted in the void volume of the column. The amount of liposome-bound protein was determined by the Bio-Rad dye binding assay, and the liposome concentration was measured by total phosphorus using molybdate method (Morrison, Anal. Biochem., 7:218–224 (1964). SDS-PAGE of the liposomes (see Example 13, below) revealed the presence of anti-HER2 Fab'-PEG-DSPE conjugate, but no free anti-HER2 Fab' in the liposome preparation. Liposome-associated protein was quantified by SDS-PAGE (see Example 13) and binding of the added Fab'-PEG-DSPE conjugate with the liposomes was expressed as percentage of the output protein/phospholipid ratio over the input protein/phospholipid ratio. The binding of Fab'-PEG-DSPE conjugate to the liposomes was 80%. The leakage of HPTS from the liposomes during incubation with the protein-PEG-DSPE conjugate to the liposomes was less than 2%.

Example 7
Preparation of immunoliposomes with conjugated anti-HER2 scFv antibodies and loaded with a fluorescent pH-sensitive indicator Using the procedure of Example 6, the conjugate of anti-HER2 single chain Fv C6.5Cys with Mal-PEG-DSPE, obtained according to Example 5, was incubated with HPTS-loaded liposomes at the input ratio of 15.6 μg of protein per 1 μmol of liposome phospholipid. After separation of unbound material by gel-filtration on Sepharose 4B, the liposomes were assayed as described in Example 6. The output protein/phospholipid ratio was 14.4 μg/ttmol, which indicated 92.3% binding of the conjugate to the liposomes.

Example 8
Uptake of the liposomes by HER2-overexpressing cells.

HER2-overexpressing human breast cancer cells (SK-BR-3) were grown in McCoy SA medium supplemented with 10% fetal calf serum, 50 U/ml of penicillin, and 50 U/ml of streptomycin at 37° C. and 5% $CO_2$. Twenty four hours prior to assay, the cells were harvested by treatment with 5 mM EDTA in phosphate buffered saline, and plated into 24-well cell culture plates at a density of 200,000 cells/well in 1 ml of cell culture medium. Liposomes were added to the cell culture medium in the wells (in triplicates) to achieve a final concentration of 25 μM of liposome phospholipids. The plates were then incubated 4 hours with gentle agitation at 37° C. and 5% $CO_2$. After incubation the media were aspirated from the wells, the cell layers were rinsed four times with 1 ml of phosphate buffered saline, harvested into 1 ml of 5 mM EDTA in phosphate buffered saline, and the amounts of cell-bound and endocytosed liposomes were determined by fluorometry as described in Kirpotin et al., *Biochemistry*, 36:66–75 (1997). For comparison, incubations were also performed with the liposomes conjugated to anti-HER2 Fab' and scFv via Mal-PEG-DSPE linkers pre-included into the liposome composition (Kirpotin et al., Ibid). The results are summarized in the following table:

| Liposomes | Proteins per liposome | Total cell-associated liposomes, nmol phospholipid/$10^6$ cells | Endocytosed liposomes, % of total |
|---|---|---|---|
| No antibody | 0 | 0.0059 ± 0.00036 | 0 |
| anti-HER2 Fab', conjugation to pre-incorporated linker | 34 | 0.744 ± 0.086 | 86 ± 7.8 |
| anti-HER2 scFv, conjugation to pre-incorporated linker | 37 | 0.311 ± 0.025 | 59.3 ± 4.3 |
| anti-HER2 Fab', according to Example 4 | 43 | 1.304 ± 0.054 | 95.9 ± 3.2 |
| anti-HER2 scFv, according to Example 5 | 39 | 0.576 ± 0.035 | 60.4 ± 0.9 |

As evidenced by these data, target cell binding and internalization of the liposomes prepared according to the present invention was at least equal, and often superior to, that of the similar liposomes prepared according to the best prior method.

Example 9
Preparation of anti-HER2 immunoliposomal doxorubicin by modification of premanufactured liposomal doxorubicin with anti HER2 Fab'-PEG-DSPE conjugate at 55° C.

0.38 ml of commercially available liposomal doxorubicin (Doxil®, Sequus Pharmaceuticals, Inc.) containing 2 mg/ml of doxorubicin was mixed with 0.26 ml of the preparation of anti HER2 Fab'-PEG-DSPE conjugate obtained according to Example 6, incubated at 55° C. for 20 min., and quickly cooled down in ice-water. Unbound material and low-molecular components were removed by gel-filtration of the incubation products through a column with Sepharose 4B (Pharmacia). The liposomes were collected in the void volume of the column, and assayed for protein using SDS-PAGE, for phospholipid using the molybate method, and for doxorubicin by spectrophotometry after solubilization in acidified isopropanol ($E^{1\%}_{480}$=208). Found: approx. 45 Fab'/liposome (77% binding of the added conjugate). The leakage of doxorubicin from liposomes was not observed (doxorubicin content prior to incubation, 145.9 μg/,mol phospholipid; after incubation, 155.8 μg/mol phospholipid).

Example 10
Preparation of anti-HER2 immunoliposomal doxorubicin by modification of premanufactured liposomal doxorubicin with anti-HER2 scFv-PEG-DSPE conjugate at 55° C.

The modification was performed as described in Example 9, using 0.4 ml of C6.5Cys-PEG-DSPE conjugate preparation (Example 5) and 0.31 ml of Doxilu. Found: 48 proteins/liposome (quantitative binding of the conjugate to liposomes); drug leakage 3.7% (doxorubicin content prior to modification, 145.9 μg/Amol phospholipid; after modification, 140.5 μg/μmol phospholipid).

Example 11
Preparation of anti-HER2 immunoliposomal doxorubicin by modification of Doxil® with anti-HER2 Fab'-PEG-DSPE conjugate at 37° C.

The modification was performed as described in Example 9 above, using 0.31 ml of Doxil® and 0.212 ml of anti-HER2 Fab'-PEG-DSPE preparation (Example 4), but the incubation was overnight at 37° C. Found: 46 Fab'/liposome (82% binding of the added conjugate to liposomes); drug leakage was not observed (doxorubicin prior to modification 145.9 μg/μmol phospholipid; after modification, 146.0 μg/μmol phospholipid). Transition temperature of the lipid constituent of Doxil® (hydrogenated soy phosphatidylcholine) is close to 55° C. Thus, modification is equally effective when the liposome lipids are in the gel state.

Example 12
Preparation of anti-HER2 immunoliposomal doxorubicin by modification of Doxil® with anti-HER2 scFv-PEG-DSPE conjugate at 37° C.

The modification was performed as described in Example 11, above, using 0.31 ml of Doxil® and 0.4 ml of C6.5Cys-PEG-DSPE conjugate preparation (Example 5). Found: 49 proteins/liposome (quantitative binding of the conjugate to liposomes). Drug leakage was not detected (doxorubicin prior to modification 145.9 μg/μmol phospholipid; after modification, 150.3.0 μg/μmol phosholipid). Thus, modification of the liposomes with scFv-PEG-DSPE conjugate was equally effective when the liposome lipids were in the gel state.

Example 13
Quantitation of antibody conjugate in the liposomes and conjugation products prepared according to Examples 6–12.

The amount of protein-PEG conjugate in the conjugation product and in the liposomes was assayed by polyacrylamide gel electrophoresis in the presence of sodium dodecylsulfate (SDS-PAGE) under non-reducing conditions according to Laemmli (1974). Typically, 5–20 μL aliquots of analytical sample were mixed with 6× sample buffer containing SDS and track dye (bromophenol blue), incubated 1 min. at 60° C., and applied onto a polyacrylamide gel (dimensions 10×10×0.075 cm) with a concentration of 10–12%, and cross-linker content of 2.6%. The separation was effected in a vertical slab gel electrophoresis apparatus at constant current of 30 mA. The protein bands were developed by Coomassie Blue staining using conventional methods. The conjugate formed a distinct band with lower electrophoretic mobility than the original protein. For quantitation of protein, the bands were excised, and the dye was extracted into 50% aqueous dimethylformamide at 100° C. for 30 min. The amount of extracted dye was quantified by spectrophotometry at 595 nm, and the protein amount per band was determined by comparison to a standard curve produced from the similarly processed bands of concomitantly run standard amounts of corresponding protein 9(Fab' or scFv).

Example 14
Delivery of doxorubicin to HER2-overexpressing cancer cells by anti-HER2 immunoliposomes prepared according to Examples 9–12.

HER2-overexpressing human breast cancer cells (SK-BR-3) were grown and plated as described in Example 8, above. Preparations of anti-HER2 immunoliposomal doxorubicin (Examples 9–12 above) were added to the cell culture medium in the wells (in triplicates) to achieve final 200 1M concentration of liposome phospholipids (0.030±0.001 mg/ml of doxorubicin). The plates were then incubated 4 hours with gentle agitation at 37° C. and 5% $CO_2$. After incubation the liquid was aspirated from the wells, the cell layers were rinsed 3 times with 1 ml each time of phosphate buffered saline, and the cells were harvested into 0.5 ml of 5 mM EDTA in phosphate buffered saline, pelleted by centrifugation, and extracted with 0.3N HC1/50% ethanol mixture. The amount of doxorubicin in ethanol-HCI extracts was determined by spectrofluorometry (excitation wavelength, 470 nm; emission wavelength 590 nm) and normalized to the quantity of plated cells. For comparison, incubations were performed also with the liposomes conjugated to anti-HER2 scFv (C6.5Cys) via Mal-PEG-DSPE linkers pre-incorporated into the liposome lipid matrix (Kirpotin et al., 1997). To assess the specificity of binding, in some wells the cells were preincubated with 5 µg of the free anti-HER2 bivalent monoclonal antibody (anti-HER2MAb). The results are summarized in the following table:

| Liposomal doxorubicin preparation: | Doxorubicin uptake, pg/cell (mean ± SE) |
|---|---|
| Example 9 | 1.652 ± 0.046 |
| Example 10 | 1.364 ± 0.016 |
| Example 11 | 1.518 ± 0.040 |
| Example 12 | 1.118 ± 0.005 |
| anti-HER2 scFv, conjugation to liposome-incorporated active linker | 0.372 ± 0.015 |
| Example 9 + anti-HER2MAb | 0.372 ± 0.015 |

Immunoliposomes prepared according to the present invention were capable of delivery of liposome-encapsulated doxorubicin to target cells even more efficiently than immunoliposomes prepared by previous methods, i.e. conjugation of the antibody fragment to the liposomes containing activated linker. Preincubation of the cells with free antibody reactive to the target antigen (HER2 protein) on the cell surface caused tenfold decrease in the uptake of immunoliposomal doxorubicin prepared according to the present invention; therefore, the uptake was target-specific.

Example 15
Preparation of lipid-DNA complex microparticles with conjugated antibody fragments A suspension of lipid-DNA microparticles (measuring 410±150 nm in size by dynamic laser scattering) composed of plasmid DNA (pCMV/IVS-Luc⁺; 10 µg/mL), dimethyl dioctadecylammonium bromide (DDAB, 60 nmol/mL), and dioleoyl phosphatidylethanolarmine (DOPE, 60 mnol/mL) in 5% aqueous dextrose, was prepared as described by Hong et al. (FEBS lett. 400:233–237, 1997). Fab'-PEG-DSPE conjugate was prepared by co-incubation of Mal-PEG-DSPE and anti-HER2 antibody Fab' fragments at a molar ratio of 4:1, at a concentration of the protein of 0.3 mg/mL in aqueous physiological buffer, at pH 7.2 for 2 hours. Lipid-DNA microparticles with conjugated anti-HER2 Fab' fragments were prepared by incubation of the lipid-DNA microparticles with the conjugate in the amount of 0.5 mol. % relative to total particle lipid content for at least 30 min. at room temperature. Control particles with linker alone (non-targeted control) were prepared in the similar manner, but non-conjugated, β-mercaptoethanol-quenched Mal-PEG-DSPE was substituted for the Fab'-PEG-DSPE conjugate.

Example 16
Targeted DNA transfection of the cells by lipid-DNA microparticles with conjugated antibody fragments Transfection activity of pCMV/IVS-Luc⁺ DNA-lipid microparticles prepared as in Example 15, above was studied in the cultures of human breast cancer cells: SK-BR-3 (overexpressing the target antigen, HER2 oncoprotein) and MCF-7 (the line with low expression of HER2). Expression of the reporter gene (luciferase) was determined by luminometry after 24-hour exposure of the cells to lipid-DNA complexes (1 µg of DNA per 50–100,000 cells) in 10% serum-supplemented growth medium, and served as the measure of transfection efficiency. The detailed description of this experimental procedure is given in Hong et al., FEBS Lett. 400:233–237 (1997). Anti-HER2 Fab' conjugated DNA-lipid microparticles prepared according to this invention were about 25-times more efficient for the plasmid delivery to target-positive SK-BR-3 cells than matching non-targeted particles. In the target-negative MCF-7 cells, targeted and nontargeted DNA-lipid particles had equal efficiency. Thus, antibody-modified lipid-DNA particles prepared according to the invention, are capable of target-specific delivery of functional DNA into human cancer cells.

| Cells: | Microparticles | Luciferase expression, ng/mg cell protein (mean ± SE) |
|---|---|---|
| SK-BR-3 | DNA/lipid alone | 116.2 ± 35.4 |
| SK-BR-3 | DNA/lipid + Mal-PEG-DSPE (*non-target control) | 40.4 ± 0.1 |
| SK-BR-3 | DNA-lipid + Fab'-PEG-DSPE (targeted) | 995 ± 197 |
| MCF-7 | DNA/lipid alone | 6.44 ± 0.34 |
| MCF-7 | DNA/lipid + Mal-PEG-DSPE (*non-target control) | 0.58 ± 0.30 |
| MCF-7 | DNA-lipid + Fab'-PEG-DSPE (targeted) | 0.71 ± 13 |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for preparing a lipidic microparticle attached to a protein by means of a linker molecule, said method comprising the step of:

incubating a lipidic microparticle with a protein conjugated to a linker molecule comprising a hydrophobic domain, a hydrophilic polymer chain terminally attached to the hydrophobic domain, and a chemical group reactive to one or more functional groups on a protein molecule and attached to the hydrophilic polymer chain at a terminus contralateral to the hydrophobic domain, for a time sufficient to permit the hydrophobic domain to become stably associated with the lipidic microparticle.

2. A method for preparing a lipidic microparticle attached to a protein, said method comprising the step of:

incubating a protein comprising a terminally appended amino acid sequence comprising primarily amino acids with hydrophilic side chains, which sequence is followed by a lipid modification site with a synthetically appended lipid moiety, with a lipidic microparticle for a time sufficient to permit the lipid moiety to become stably associated with the lipidic microparticle.

3. The method of claim 1, wherein the lipidic microparticle is a liposome.

4. The method of claim 1, wherein the lipidic microparticle is a lipid:nucleic acid complex.

5. The method of claim 1, wherein the lipidic microparticle is a lipid:drug complex.

6. The method of claim 1, wherein the lipidic microparticle is a microemulsion droplet.

7. The method of claim 1, wherein the protein is an antibody.

8. The method of claim 1, wherein the protein is an Fab' fragment of an antibody.

9. The method of claim 1, wherein the protein is single chain Fv antibody.

10. The method of claim 1, wherein the protein is an enzyme.

11. The method of claim 1, wherein the protein is a hormone.

12. The method of claim 1, wherein the protein is a growth factor.

13. The method of claim 1, wherein the protein is a nucleic acid binding protein.

14. The method of claim 1, wherein the reactive group is a maleimido group.

15. The method of claim 1, wherein the incubation occurs in an aqueous medium.

16. The method of claim 1, wherein the conjugated protein undergoes a purification step to separate it from unreacted linker and unmodified protein prior to incubation.

17. The method of claim 16, wherein the purification step is selected from the group consisting of salting-out, dialysis, and chromatography.

18. A lipidic microparticle conjugated to a protein by the method of claim 1, wherein the protein is conjugated to the lipidic microparticle through a linker molecule by means of a chemical group, which chemical group prior to conjugation is reactive with a component of said lipidic microparticle.

19. A liposome conjugated to a protein by the method of claim 1, wherein the protein is conjugated to the liposome through a linker molecule by means of a chemical group, which chemical group prior to conjugation is reactive with a component of said liposome.

20. A lipid:nucleic acid complex conjugated to a protein by the method of claim 1.

21. A lipid:drug complex conjugated to a protein by the method of claim 1, wherein the protein is conjugated to the lipid:drug complex through a linker molecule by means of a chemical group, which chemical group prior to conjugation is reactive with a component of said lipid:drug complex.

22. A microemulsion droplet conjugated to a protein by the method of claim 1, wherein the protein is conjugated to the microemulsion droplet through a linker molecule by means of a chemical group, which chemical group prior to conjugation is reactive with a component of said microemulsion droplet.

23. A lipid:nucleic acid complex conjugated to a protein by the method of claim 1, wherein the protein is conjugated to the lipid:nucleic acid complex through a linker molecule by means of a chemical group, which chemical group prior to conjugation is reactive with a component of said lipid:nucleic acid complex.

24. A lipidic microparticle conjugated to a protein, wherein the protein is conjugated to the lipidic microparticle through a linker molecule comprising a hydrophobic domain, a hydrophilic polymer chain terminally attached to the hydrophobic domain, and a chemical group reactive to one or more functional groups on a protein molecule and attached to the hydrophilic polymer chain at a terminus contralateral to the hydrophobic domain, wherein the chemical group prior to conjugation is reactive with a component of said lipidic microparticle.

25. A lipidic microparticle of claim 24, wherein the lipidic microparticle is selected from the group consisting of: a liposome, a lipid:nucleic acid complex, a lipid:drug complex, and a microemulsion droplet.

26. A lipidic microparticle conjugated to a protein by the method of claim 1, wherein the microparticle does not bear unconjugated linkers.

27. A liposome conjugated to a protein by the method of claim 1, wherein the microparticle does not bear unconjugated linkers.

28. A lipid:nucleic acid complex conjugated to a protein by the method of claim 1, wherein the microparticle does not bear unconjugated linkers.

29. A lipid:drug complex conjugated to a protein by the method of claim 1, wherein the microparticle does not bear unconjugated linkers.

30. A microemulsion droplet conjugated to a protein by the method of claim 1, wherein the microparticle does not bear unconjugated linkers.

31. A lipidic microparticle conjugated to a protein through a linker molecule comprising a hydrophobic domain, a hydrophilic polymer chain terminally attached to the hydrophobic domain, and a chemical group reactive to one or more functional groups on a protein molecule and attached to the hydrophilic polymer chain at a terminus contralateral to the hydrophobic domain, wherein the lipidic microparticle does not bear unconjugated linkers.

32. A lipidic microparticle of claim 31, wherein the lipidic microparticle is selected from the group consisting of: a liposome, a lipid:nucleic acid complex, a lipid:drug complex, and a microemulsion droplet.

33. A microparticle which is conjugated to two or more protein species by the method of claim 1, wherein the protein species are conjugated to the microparticle through a functional group, which functional group is the same for each protein species.

34. A liposome which is conjugated to two or more protein species by the method of claim 1, wherein the protein species are conjugated to the liposome through a functional group, which functional group is the same for each protein species.

35. A lipid:nucleic acid complex which is conjugated to two or more protein species by the method of claim 1, wherein the protein species are conjugated to the lipid:nucleic acid complex through a functional group, which functional group is the same for each protein species.

36. A lipid:drug complex which is conjugated to two or more protein species by the method of claim 1, wherein the proteins are conjugated to the lipid:drug complex through a functional group, which functional group is the same for each protein species.

37. A microemulsion droplet which is conjugated to two or more protein species by the method of claim 1, wherein the proteins are conjugated to the microemulsion droplet through a functional group, which functional group is the same for each protein species.

38. A lipidic microparticle which is conjugated to two or more protein species, wherein the protein species are conjugated to the lipidic microparticle through linker molecules, each linker molecule comprising a hydrophobic domain, a hydrophilic polymer chain terminally attached to the hydrophobic domain, and a chemical group reactive to one or more functional groups on said protein molecule conjugated to said linker, and attached to the hydrophilic polymer chain at a terminus contralateral to the hydrophobic domain, which functional groups are the same for each protein species.

39. A lipidic microparticle of claim 38, wherein the lipidic microparticle is selected from the group consisting of: a liposome, a lipid:nucleic acid complex, a lipid:drug complex, and a microemulsion droplet.

40. A method of claim 1, wherein two or more protein species are attached to said lipidic microparticle.

41. A method of claim 40, wherein said protein species are independently selected from the group consisting of: an antibody, an Fab', and a single-chain Fv antibody.

42. A method of claim 40, wherein said lipidic microparticle is a liposome.

43. A method for attaching a plurality of protein species to a lipidic microparticle, wherein at least one of the protein species is attached by the method of claim 1.

44. A method of claim 1, wherein the chemical group reactive to one or more functional groups on said protein is reactive to a component of the lipidic microparticle.

45. A method of claim 44, wherein the lipidic microparticle is selected from the group consisting of: a liposome, a lipid:nucleic acid complex, a lipid:drug complex, and a microemulsion droplet.

46. A method of claim 44, wherein the chemical group is selected from the group consisting of: an amino group, a carboxy group, a thiol group, a malemido group, an iodoacetamido group, a vinylsulfone group, an aldehyde group, a hydrazine group, a ketone group, and a cyanure chloride group.

* * * * *